(12) United States Patent
Bodduluri et al.

(10) Patent No.: US 12,178,513 B2
(45) Date of Patent: Dec. 31, 2024

(54) METHODS AND SYSTEMS FOR DIRECTING MOVEMENT OF A TOOL IN HAIR TRANSPLANTATION PROCEDURES

(71) Applicant: Venus Concept Inc., San Jose, CA (US)

(72) Inventors: (Radhika) Mohan Bodduluri, Palo Alto, CA (US); Hui Zhang, San Jose, CA (US)

(73) Assignee: Venus Concept Inc., Toronto (CA)

( * ) Notice: Subject to any disclaimer, the term of this patent is extended or adjusted under 35 U.S.C. 154(b) by 1118 days.

(21) Appl. No.: 16/259,079

(22) Filed: Jan. 28, 2019

(65) Prior Publication Data

US 2019/0151028 A1 May 23, 2019

Related U.S. Application Data

(63) Continuation of application No. 15/288,065, filed on Oct. 7, 2016, now Pat. No. 10,188,466, which is a
(Continued)

(51) Int. Cl.
*A61B 34/10* (2016.01)
*A61B 17/3205* (2006.01)
(Continued)

(52) U.S. Cl.
CPC ........ *A61B 34/10* (2016.02); *A61B 17/32053* (2013.01); *A61B 17/3468* (2013.01);
(Continued)

(58) Field of Classification Search
CPC .......... A61B 17/32053; A61B 17/3468; A61B 2017/00057; A61B 2017/00752;
(Continued)

(56) References Cited

U.S. PATENT DOCUMENTS

| | | |
|---|---|---|
| 2,667,879 A | 2/1954 | Mann |
| 3,515,128 A | 6/1970 | McEvoy |

(Continued)

FOREIGN PATENT DOCUMENTS

| | | |
|---|---|---|
| CN | 101277657 | 10/2008 |
| CN | 101506825 | 8/2009 |

(Continued)

OTHER PUBLICATIONS

"Geometric Design and Fabrication of Developable Bezier and 8-Spline Surfaces". R.M.C. Bodduluri and 8. Ravani. Transactions of the ASME. vol. 116, Dec. 1994. p.p. 1042-1048 (7 pages).

(Continued)

*Primary Examiner* — Michael T Rozanski
(74) *Attorney, Agent, or Firm* — Foley & Lardner LLP

(57) ABSTRACT

Methods and systems are provided useful in various procedures, including hair harvesting and implantation, and further including computer-implemented and/or robotic hair transplantation. Methodologies are provided which enable selection of follicular unit harvesting or implanting sites within the same row in a direction of travel of the tool, or by incrementing to another row. In various cases, such selection may be made using a lowest and closest method, overlap-based methods, position-based methods, pattern-based methods, and/or a combination of these methods. In various combinations of the methods, the output selection from one of the methods may be used as an input for one of the other methods.

18 Claims, 18 Drawing Sheets

Related U.S. Application Data continuation of application No. 13/796,159, filed on Mar. 12, 2013, now Pat. No. 9,498,289, which is a continuation-in-part of application No. 13/174,721, filed on Jun. 30, 2011, now Pat. No. 8,911,453.

(60) Provisional application No. 61/425,571, filed on Dec. 21, 2010.

(51) Int. Cl.
| | |
|---|---|
| *A61B 17/34* | (2006.01) |
| *A61B 34/30* | (2016.01) |
| *A61B 90/00* | (2016.01) |
| *A61B 17/00* | (2006.01) |
| *A61B 17/32* | (2006.01) |
| *A61B 34/00* | (2016.01) |
| *A61B 34/20* | (2016.01) |

(52) U.S. Cl.
CPC ............ *A61B 34/30* (2016.02); *A61B 90/361* (2016.02); *A61B 2017/00057* (2013.01); *A61B 2017/00752* (2013.01); *A61B 2017/320052* (2013.01); *A61B 2034/107* (2016.02); *A61B 2034/2055* (2016.02); *A61B 34/25* (2016.02); *A61B 90/37* (2016.02); *A61B 2090/3904* (2016.02); *A61B 2090/3937* (2016.02)

(58) Field of Classification Search
CPC .. A61B 2017/320052; A61B 2034/107; A61B 2034/2055; A61B 2090/3904; A61B 2090/3937; A61B 34/10; A61B 34/25; A61B 34/30; A61B 90/361; A61B 90/37
See application file for complete search history.

(56) References Cited

U.S. PATENT DOCUMENTS

| | | |
|---|---|---|
| 3,867,942 A | 2/1975 | Aseff, Jr. |
| 3,887,942 A | 6/1975 | Horowitz |
| 3,998,230 A | 12/1976 | Miller |
| 4,004,592 A | 1/1977 | Yamada |
| 4,126,124 A | 11/1978 | Miller |
| 4,160,453 A | 7/1979 | Miller |
| 4,451,254 A | 5/1984 | Dinius et al. |
| 4,475,864 A | 10/1984 | Patacca et al. |
| 4,476,864 A | 10/1984 | Tezel |
| 4,479,291 A | 10/1984 | Yamada |
| 4,598,311 A | 7/1986 | Bellina |
| 4,716,901 A | 1/1988 | Jackson et al. |
| 4,751,927 A | 6/1988 | Yamada |
| 4,768,517 A | 9/1988 | Joachim |
| 4,807,163 A | 2/1989 | Gibbons |
| 4,969,903 A | 11/1990 | Valle |
| 4,969,963 A | 11/1990 | Honkura et al. |
| 4,980,971 A | 1/1991 | Bartschat et al. |
| 5,029,220 A | 7/1991 | Juday |
| 5,036,860 A | 8/1991 | Leigh et al. |
| 5,036,880 A | 8/1991 | Safford et al. |
| 5,050,608 A | 9/1991 | Watanabe et al. |
| 5,078,140 A | 1/1992 | Kwoh |
| 5,090,745 A | 2/1992 | Kluger |
| 5,183,053 A | 2/1993 | Yeh et al. |
| 5,207,671 A | 5/1993 | Franken et al. |
| 5,230,623 A | 7/1993 | Guthrie et al. |
| 5,251,127 A | 10/1993 | Raab |
| 5,331,472 A | 7/1994 | Rassman |
| 5,395,368 A | 3/1995 | Ellman et al. |
| 5,417,683 A | 5/1995 | Shiao |
| 5,439,475 A | 8/1995 | Bennett |
| 5,449,370 A | 9/1995 | Vaitekunas |
| 5,483,961 A | 1/1996 | Kelly et al. |
| 5,490,850 A | 2/1996 | Ellman et al. |
| 5,562,613 A | 10/1996 | Kaldany |
| 5,578,054 A | 11/1996 | Arnold |
| 5,584,841 A | 12/1996 | Rassman |
| 5,584,851 A | 12/1996 | Banuchi |
| 5,591,186 A | 1/1997 | Wurster et al. |
| 5,611,810 A | 3/1997 | Arnold et al. |
| 5,611,811 A | 3/1997 | Goldberg |
| 5,662,661 A | 9/1997 | Boudjema |
| 5,693,064 A | 12/1997 | Arnold |
| 5,733,278 A | 3/1998 | Slatkine et al. |
| 5,749,362 A | 5/1998 | Funda et al. |
| 5,782,843 A | 7/1998 | Aasberg |
| 5,782,851 A | 7/1998 | Rassman |
| 5,782,853 A | 7/1998 | Zeevi et al. |
| 5,792,163 A | 8/1998 | Hitzig |
| 5,792,169 A | 8/1998 | Markman |
| 5,811,810 A | 9/1998 | Hellemans et al. |
| 5,817,105 A | 10/1998 | Van Der Brug |
| 5,817,120 A | 10/1998 | Rassman |
| 5,827,217 A | 10/1998 | Silver et al. |
| 5,827,297 A | 10/1998 | Boudjema |
| 5,836,938 A | 11/1998 | Slatkine |
| 5,858,019 A | 1/1999 | Ashraf |
| 5,865,744 A | 2/1999 | Lemelson |
| 5,873,888 A | 2/1999 | Costanzo |
| 5,893,853 A | 4/1999 | Arnold |
| 5,895,403 A | 4/1999 | Collinsworth |
| 5,899,916 A | 5/1999 | Casparian |
| 5,899,918 A | 5/1999 | Knott et al. |
| 5,901,199 A | 5/1999 | Murphy et al. |
| 5,951,572 A | 9/1999 | Markman |
| 5,961,529 A | 10/1999 | Arnold |
| 5,984,915 A | 11/1999 | Loeb et al. |
| 5,984,936 A | 11/1999 | Mangubat et al. |
| 5,989,273 A | 11/1999 | Arnold |
| 5,989,279 A | 11/1999 | Rassman |
| 5,997,550 A | 12/1999 | Russell |
| 6,013,087 A | 1/2000 | Adams et al. |
| 6,027,512 A | 2/2000 | Bridges |
| 6,056,736 A | 5/2000 | Markman |
| 6,059,807 A | 5/2000 | Boudjema |
| 6,110,189 A | 8/2000 | Markman |
| 6,110,195 A | 8/2000 | Xie et al. |
| 6,120,521 A | 9/2000 | Casparian |
| 6,162,212 A | 12/2000 | Kreindel et al. |
| 6,228,075 B1 | 5/2001 | Furumoto |
| 6,241,687 B1 | 6/2001 | Voegele et al. |
| 6,306,142 B1 | 10/2001 | Johanson et al. |
| 6,341,831 B1 | 1/2002 | Weber et al. |
| 6,347,240 B1 | 2/2002 | Foley et al. |
| 6,405,072 B1 | 6/2002 | Cosman |
| 6,417,641 B2 | 7/2002 | Peless et al. |
| 6,434,416 B1 | 8/2002 | Mizoguchi et al. |
| 6,445,943 B1 | 9/2002 | Ferre et al. |
| 6,461,369 B1 | 10/2002 | Kim |
| 6,470,236 B2 | 10/2002 | Ohtsuki |
| 6,484,049 B1 | 11/2002 | Seeley et al. |
| 6,547,782 B1 | 4/2003 | Taylor |
| 6,554,825 B1 | 4/2003 | Murray et al. |
| 6,572,625 B1 | 6/2003 | Rassman |
| 6,585,746 B2 | 7/2003 | Gildenberg |
| 6,632,218 B1 | 10/2003 | Furumoto et al. |
| 6,694,167 B1 | 2/2004 | Ferre et al. |
| 6,717,102 B2 | 4/2004 | Neev et al. |
| 6,771,840 B1 | 8/2004 | Ioannou et al. |
| 6,885,912 B2 | 4/2005 | Peless et al. |
| 6,887,209 B2 | 5/2005 | Kadziauskas et al. |
| 6,916,316 B2 | 7/2005 | Jay |
| 6,917,702 B2 | 7/2005 | Beardsley |
| 6,973,202 B2 | 12/2005 | Mostafavi |
| 6,973,931 B1 | 12/2005 | King |
| 7,083,611 B2 | 8/2006 | Lemchen |
| 7,127,081 B1 | 10/2006 | Erdem |
| 7,144,406 B2 | 12/2006 | Pak et al. |
| 7,172,604 B2 | 2/2007 | Cole |
| 7,175,617 B2 | 2/2007 | Jay |
| 7,201,722 B2 | 4/2007 | Krueger |
| 7,206,627 B2 | 4/2007 | Abovitz et al. |
| 7,217,266 B2 | 5/2007 | Anderson et al. |
| 7,231,063 B2 | 6/2007 | Naimark et al. |

(56) References Cited

U.S. PATENT DOCUMENTS

| | | | |
|---|---|---|---|
| 7,277,120 B2 | 10/2007 | Gere et al. | |
| 7,318,805 B2 | 1/2008 | Schweikard et al. | |
| 7,383,073 B1 | 6/2008 | Abovitz et al. | |
| 7,426,318 B2 | 9/2008 | Fu et al. | |
| 7,477,782 B2 | 1/2009 | Qureshi et al. | |
| 7,539,334 B2 | 5/2009 | Corrion | |
| 7,553,308 B2 | 6/2009 | Jay | |
| 7,611,452 B2 | 11/2009 | Allison et al. | |
| 7,613,337 B2 | 11/2009 | Corrion | |
| 7,621,934 B2 | 11/2009 | Bodduluri et al. | |
| 7,623,702 B2 | 11/2009 | Arata et al. | |
| 7,627,157 B2 | 12/2009 | Qureshi et al. | |
| 7,713,205 B2 | 5/2010 | Fu et al. | |
| 7,756,567 B2 | 7/2010 | Kuduvalli et al. | |
| 7,894,649 B2 | 2/2011 | Fu et al. | |
| 7,967,016 B2 | 6/2011 | Anderson et al. | |
| 8,690,894 B2 | 4/2014 | Bodduluri et al. | |
| 8,911,453 B2 * | 12/2014 | Tenney | A61B 34/30 606/133 |
| 9,364,684 B2 | 6/2016 | Poran et al. | |
| 9,498,289 B2 * | 11/2016 | Zhang | A61B 17/32053 |
| 9,526,581 B2 | 12/2016 | Bodduluri et al. | |
| 9,743,988 B2 * | 8/2017 | Tenney | A61B 34/30 |
| 10,188,466 B2 * | 1/2019 | Zhang | A61B 34/10 |
| 2001/0034534 A1 | 10/2001 | Transue | |
| 2002/0085668 A1 | 7/2002 | Blumhofer et al. | |
| 2002/0103500 A1 | 8/2002 | Gildenberg | |
| 2002/0133149 A1 | 9/2002 | Bessette | |
| 2002/0151784 A1 | 10/2002 | Mizoguchi et al. | |
| 2003/0040766 A1 | 2/2003 | Werner | |
| 2003/0040788 A1 | 2/2003 | Dupelle et al. | |
| 2003/0060810 A1 | 3/2003 | Syrowicz et al. | |
| 2003/0097144 A1 | 5/2003 | Lee | |
| 2003/0120298 A1 | 6/2003 | Gildenberg | |
| 2003/0125622 A1 | 7/2003 | Schweikard et al. | |
| 2003/0181801 A1 | 9/2003 | Lasser et al. | |
| 2003/0181936 A1 | 9/2003 | Trautman et al. | |
| 2003/0212320 A1 | 11/2003 | Wilk et al. | |
| 2004/0034282 A1 | 2/2004 | Quaid et al. | |
| 2004/0092824 A1 | 5/2004 | Stamnes et al. | |
| 2004/0092924 A1 | 5/2004 | Vasa | |
| 2004/0116942 A1 | 6/2004 | Feller | |
| 2004/0162505 A1 | 8/2004 | Kaplan et al. | |
| 2004/0193203 A1 | 9/2004 | Pak et al. | |
| 2004/0197728 A1 | 10/2004 | Abolfathi et al. | |
| 2004/0204700 A1 | 10/2004 | Weaver et al. | |
| 2004/0204760 A1 | 10/2004 | Fitz et al. | |
| 2004/0220589 A1 | 11/2004 | Feller | |
| 2004/0225314 A1 | 11/2004 | Fukuyama | |
| 2004/0243147 A1 | 12/2004 | Lipow | |
| 2005/0004592 A1 | 1/2005 | Criscuolo | |
| 2005/0018885 A1 | 1/2005 | Chen et al. | |
| 2005/0096515 A1 | 5/2005 | Geng | |
| 2005/0096687 A1 | 5/2005 | Rassman et al. | |
| 2005/0119783 A1 | 6/2005 | Brisson et al. | |
| 2005/0187573 A1 | 8/2005 | Rassman et al. | |
| 2005/0228256 A1 | 10/2005 | Labadie et al. | |
| 2005/0245952 A1 | 11/2005 | Feller | |
| 2005/0267506 A1 | 12/2005 | Harris | |
| 2006/0020370 A1 | 1/2006 | Abramson | |
| 2006/0079816 A1 | 4/2006 | Barthe et al. | |
| 2006/0127881 A1 | 6/2006 | Wong et al. | |
| 2006/0161179 A1 | 7/2006 | Kachenmeister | |
| 2006/0178678 A1 | 8/2006 | Cole | |
| 2006/0293598 A1 | 12/2006 | Fraser | |
| 2006/0293703 A1 | 12/2006 | Pak et al. | |
| 2007/0038236 A1 | 2/2007 | Cohen | |
| 2007/0078466 A1 * | 4/2007 | Bodduluri | A61B 90/36 606/133 |
| 2007/0106306 A1 | 5/2007 | Bodduluri et al. | |
| 2007/0150247 A1 | 6/2007 | Bodduluri | |
| 2007/0255293 A1 | 11/2007 | Corre | |
| 2007/0293884 A9 | 12/2007 | Cole et al. | |
| 2008/0002809 A1 | 1/2008 | Bodduluri | |
| 2008/0004603 A1 | 1/2008 | Larkin et al. | |
| 2008/0004633 A1 | 1/2008 | Arata et al. | |
| 2008/0010705 A1 | 1/2008 | Quaid et al. | |
| 2008/0010706 A1 | 1/2008 | Moses et al. | |
| 2008/0033410 A1 | 2/2008 | Rastegar et al. | |
| 2008/0144908 A1 | 6/2008 | West et al. | |
| 2008/0154247 A1 | 6/2008 | Dallarosa et al. | |
| 2008/0177287 A1 | 7/2008 | Rassman et al. | |
| 2008/0202200 A1 | 8/2008 | West | |
| 2008/0234697 A1 | 9/2008 | Dubois | |
| 2008/0242990 A1 | 10/2008 | Zanelli et al. | |
| 2008/0247637 A1 | 10/2008 | Gildenberg | |
| 2009/0000306 A1 | 1/2009 | Damle et al. | |
| 2009/0003523 A1 | 1/2009 | Raanes et al. | |
| 2009/0003528 A1 | 1/2009 | Ramraj et al. | |
| 2009/0005677 A1 | 1/2009 | Weber et al. | |
| 2009/0099559 A1 | 4/2009 | Dhadwal | |
| 2009/0129545 A1 | 5/2009 | Adler et al. | |
| 2009/0230269 A1 | 9/2009 | Dallarosa | |
| 2009/0232026 A1 | 9/2009 | Lu | |
| 2009/0299477 A1 | 12/2009 | Clayton et al. | |
| 2009/0306680 A1 * | 12/2009 | Qureshi | A61B 90/361 606/133 |
| 2009/0314925 A1 | 12/2009 | Van Vorhis et al. | |
| 2009/0324078 A1 | 12/2009 | Wu et al. | |
| 2009/0326322 A1 | 12/2009 | Diolaiti | |
| 2009/0326553 A1 | 12/2009 | Mustufa et al. | |
| 2010/0080415 A1 | 4/2010 | Qureshi et al. | |
| 2010/0080417 A1 * | 4/2010 | Qureshi | G16H 50/20 700/59 |
| 2010/0125287 A1 | 5/2010 | Cole et al. | |
| 2010/0166323 A1 | 7/2010 | Zhao et al. | |
| 2010/0228163 A1 | 9/2010 | Gildenberg | |
| 2010/0234871 A1 | 9/2010 | Qureshi et al. | |
| 2010/0245541 A1 | 9/2010 | Zhao et al. | |
| 2010/0256504 A1 | 10/2010 | Moreau-Gaudry et al. | |
| 2011/0098553 A1 | 4/2011 | Robbins et al. | |
| 2011/0116703 A1 | 5/2011 | Fu et al. | |
| 2011/0160589 A1 | 6/2011 | Fu et al. | |
| 2012/0158019 A1 | 6/2012 | Tenney et al. | |
| 2013/0237973 A1 | 9/2013 | Kim et al. | |
| 2013/0239737 A1 | 9/2013 | Fuller | |
| 2016/0193035 A1 | 7/2016 | Silva Ramos et al. | |
| 2016/0324586 A1 | 11/2016 | Zingaretti et al. | |
| 2017/0354472 A1 * | 12/2017 | Tenney | A61B 34/30 |

FOREIGN PATENT DOCUMENTS

| | | |
|---|---|---|
| CN | 101523426 | 9/2009 |
| DE | 10249786 | 5/2004 |
| EP | 0 524 454 A1 | 1/1993 |
| JP | 08-227454 | 9/1996 |
| JP | H55-227454 A | 9/1996 |
| JP | 2000-245525 | 9/2000 |
| JP | 2002-011106 | 1/2002 |
| JP | 2002-083318 | 3/2002 |
| JP | 2013-027684 | 2/2013 |
| KR | 20008/0049793 | 6/2008 |
| KR | 20080049793 | 6/2008 |
| WO | WO-98/25666 A1 | 6/1998 |
| WO | WO-99/27863 | 6/1999 |
| WO | WO-00/64379 | 11/2000 |
| WO | WO-2006/021040 | 3/2006 |
| WO | WO-2007/041014 | 4/2007 |
| WO | WO-2007/041267 | 4/2007 |
| WO | WO-2007/059164 | 5/2007 |
| WO | WO-2008/024955 | 2/2008 |
| WO | WO-2008/043091 | 4/2008 |
| WO | WO-2008/109284 | 9/2008 |
| WO | WO-2008/156838 | 12/2008 |
| WO | WO-2010/036513 | 4/2010 |

OTHER PUBLICATIONS

Anthony R. Lanfranco; Andres E. Castellanos; Jaydev P. Desai; William C. Meyers, "Robotic Surgery: A Current Perspective," Annals of Surgery, vol. 239, No. 1, Jan. 2004, pp. 14-21.
Computerworld. "Dispatches & Images from the Fringes of the Electronic Frontier". Mar. 30, 1998, Nexis, p. 1.

(56) References Cited

OTHER PUBLICATIONS

Fosyth, et al., "Computer Vision, A Modern Approach", 2003, Cover, Cover page, Publication page and Chapter17, pp. 373-397, 25 pages.
Inaba, et al., "Androgenetic Alopecia, Modern Concepts of Pathogenesis and Treatment, 29. Operative Treatment for Androgenetic Alopecia.", 1996, pp. 233-234.
Jain, et al., "Machine Vision", 1995, Cover page, Publication page, and Chapter 12.3, pp. 320-325, 5 pages.
Jain, et al., "Machine Vision", 1995, Cover Page, Publication page, and Chapter 14, pp. 406-453, 50 pages.
John Iselin Woodfill, Gaile Gordon, Dave Jurasek, Terrance Brown, Ron Buck, "The Tyzx DeepSea G2 Vision System, A Taskable, Embedded Stereo Camera," Proceedings of the IEEE Computer Society Workshop on Embedded Computer Vision, Conference on Computer Vision and Pattern Recognition, Jun. 2006, pp. 1-7.
John Iselin Woodfill, Gaile Gordon, Ron Buck, "Tyzx DeepSea High Speed Stereo Vision System," Proceedings of the IEEE Computer Society Workshop on Real Time 3-0 Sensors and Their Use, Conference on Computer Vision and Pattern Recognition, Jun. 2004, pp. 1-5.
John Iselin Woodfill, Gaile Gordon, Ron Buck, "Tyzx DeepSea High Speed Stereo Vision System," Proceedings of the IEEE Computer Society Workshop on Real Time 3-D Sensors and Their Use, Conference on Computer Vision and Pattern Recognition, Jun. 2004, pp. 1-5.
Ko, et al., "Fast Digital Image Stabilizer Based on Gray-Coded Bit-Plane Matching", Consumer Electronics, ICCE International Conference on Jun. 22-24, 1999, pp. 90-91, 2 pages ? EFSWeb2.1.17.
Kurt Konolige and David Beymer, SRI International, "SRI Small Vision System," User's Manual Sep. 2005 (88 pages).
Lumenis, "VersaPulse PowerSuite Lasers", Product Brochure.
Mandt, et al.; "Epilation Today: Physiology of the Hair Follicle and Clinical Photo-Epilation", Journal of Investigative Dermatology Symposium Proceedings (2005) 10, 2005, pp. 271-274.
Marshall, "Semiconductor-Based Lasers in Medicine", Lasers and Electro-Optics Society Annual Meeting, 1998. LEOS '98. vol. 2, Dec. 1-4, 1998 p. 339, Dec. 1998, p. 339.
Mohammed Alhaddab, MD; Thomas Kohn, MD; and Mark Sidloi, BSc. Effect of Graft Size, Angle, and Intergraft Distance on Dense Packing in Hair Transplant. Dermatol Surg 2005; 31: pp. 650-654. Published by BC Decker Inc.
Robert M. Bernstein, MD; William R. Rassman, MD; Wojciech Szaniawski, MD and Alan J Halperin, MD. "Follicular Transplantation" Int. Journal of Aesthetic and Restoration Surgery, vol. 3, No. 2, 1995, pp. 119-132.
Rolf Hoffmann and Dominique Van Neste. "Recent Findings with Computerized Methods for Scalp Hair Growth Measurements". J Investig Dermatol Symp Proc 10: pp. 285-288, 2005.
Ronald Shapiro, MD. "Principles and techniques used to create a natural hairline in surgical hair restoration", Facial Plast Surg Clin N Am 12 (2004) pp. 201-217.
Sadick, "Laser Hair Removal", Facial Plast Surg Clin N. Am 12 (2004), pp. 191-200.
Sun, et al., "Real-Time Digital Image Stabilization Algorithm on PC", Proc SPIE vol. 4925. pp 510-513. Sep. 2002 (Abstract in English), Sep. 2002, 2 pages.
The New York Times, Monday, Sep. 15, 2003. "Implanting Hair is Tedious, Exacting Work—the Perfect Work for a Robot."
Vella, et al., "Robust Digital Image Stabilization Algorithm Using Block, Motion Vectors", Consumer Electronics, 2002 ICCE, 2002 Digest of Technical Papers, International Conference on Jun. 18-20, 2002. pp. 234-235, 2 pages.
Website, http://www.medicamat.com/materiel/hair-transplant/omnigraft/case-study.html?L=1, Omnigraft, Medicamat, Medical and Surgical Devices, Cosmetic Products, Hair Transplant/Omnigraft/Case Study, @ 2007, corresponding webpage archived Aug. 7, 2008, available at https://web.archive.org/web/20080807161016/http://www.medicamat.com/materiel/transplantation-capillaire/omnigraft/etude-clinique.html.
Website, http://www.medicamat.com/materiel/hair-transplant/punchhairmatic/case-study.html?L=1, Medicamat, Medical and Surgical Devices, Cosmetic Products, Hair Transplant/Punch Hair Matic/Case Study, corresponding webpage archived Aug. 7, 2008, available at https://web.archive.org/web/20080807160738/http://www.medicamat.com/materiel/transplantation- capillaire/punchhairmatic/etude-clinique.html (accessed Jun. 7, 2023).
William R. Rassman, MD and Sharon Carson, BA. "Micrografting in Extensive Quantities". http://www.newhair.com/resources/mp-1995-micrografting.asp (7 pages).
Woodfill, et al., "The Tyzx DeepSea G2 Vision System, A Taskable, Embedded Stereo Camera", Proceedings of the IEEE Computer Society Workshop on Embedded Computer Vision, Conference on Computer Vision and Pattern Recognition, Jun. 2006, 5 pages.
Zenzie, et al., "Super Long Pulse Hair Removal", Laser and Electro-Optics Society 2000 Annual Meeting, LEOS 2000. 13th Annual Meeting.IEEE vol. 1, Nov. 13-16, 2000, Nov. 2000, pp. 208-209.
Zenzie, et al; "Super Long Pulse Hair Removal", Laser and Electro-Optics Society 2000 Annual Meeting, LEOS 2000. 13th Annual Meeting, IEEE, vol. 1, Nov. 13-16, 2000, pp. 208-209.

* cited by examiner

910

910

METHODS AND SYSTEMS FOR DIRECTING MOVEMENT OF A TOOL IN HAIR TRANSPLANTATION PROCEDURES

RELATED APPLICATIONS

This application is a continuation of co-pending U.S. application Ser. No. 15/288,065, filed Oct. 7, 2016, which is a continuation of U.S. application Ser. No. 13/796,159, filed Mar. 12, 2013 (now U.S. Pat. No. 9,498,289), which is a continuation-in-part of U.S. application Ser. No. 13,174,721, filed Jun. 30, 2011 (now U.S. Pat. No. 8,911,453) titled "Methods and Systems for Directing Movement of a Tool in Hair Transplantation Procedures," which in turn claims priority under 35 U.S.C. 119(e) to U.S. Provisional Application No. 61/425,571 filed Dec. 21, 2010, entitled "Methods and Systems for Directing Movement of a Tool in Hair Transplantation Procedures;" the disclosures of which are hereby incorporated by reference, in their entireties.

FIELD OF THE INVENTION

The present application relates generally to hair transplantation procedures and more particularly to methods and systems used for operating a tool to harvest or implant follicular units from or into a body surface using imaging and processing techniques.

BACKGROUND OF THE INVENTION

During medical operative procedures on a patient, particularly if the procedure is of a significant duration of time, it is inevitable that patient movement and/or interruptions may occur. These interruptions may be mechanical, electrical, hardware, software, or medical in nature, or caused by some other means. For example, it may be desirable or simply unavoidable that the patient alters his/her position during the procedure, or that the patient and/or physician temporarily leave the place in which the operation is being carried out before returning. This is relevant to various medical, including cosmetic, procedures, and particularly relevant, for example, for the case of a patient undergoing a hair transplantation procedure, having follicular units harvested from a donor area (e.g., on the patient's scalp) for transplantation, or having follicular units implanted into a recipient area (e.g., a bald area on the patient's scalp). These procedures typically take several or more hours to perform. In some instances, the patient may remain in the operation chair but need to alter their position due to discomfort and/or fatigue, or simply moves due to breathing or other natural movements. In other instances the patient may need to interrupt the procedure to temporarily leave the chair.

SUMMARY OF THE INVENTION

In accordance with one general aspect, the present application discloses systems and methods for directing movement and operation of a tool in medical procedures which are at least partially automated. In some embodiments, a method of operating a tool to perform a medical procedure is provided. The method may comprise recording first locations of a plurality of fiducials appearing in one or more images; updating and recording the updated locations of at least some of the plurality of the fiducials in an updated one or more images; determining an offset of the updated locations of the at least some of the plurality of the fiducials relative to their first locations; selecting a site on which to perform the medical procedure based at least in part on the determined offset. The method may further comprise instructing the tool to perform the procedure at the selected procedure site (for example, a tattoo placement or tattoo removal procedure, or a cosmetic injection procedure, ablation procedure, eye treatment procedure, or any other procedure that could benefit from the inventions described herein); and may also comprise recording a location of the performed medical procedure.

In some embodiments the method may further comprise determining a boundary of an area on a body surface where a procedure is performed, for example, an area from which follicular units are to be harvested, or into which follicular units are to be implanted, and instructing a tool to perform an operation, such as in the example of hair transplantation to harvest from a selected harvesting site or implant into a selected implant site, for example, within or outside the determined boundary. The boundary may be determined based on a reference, for example, a plurality of fiducials, which may comprise a set of distinctive fiducials. In some embodiments, with reference to hair transplantation, the selection of follicular unit harvesting or implanting sites may take into account limitations of the tool. In those embodiments where the boundary of the area is determined, such boundary may be adjusted to eliminate portions, for example, where a tool used in the procedure has limited or insufficient access for proper operation, or to take into account one or more parameters of a skin tensioning device, if such device is used, and/or the tool. In the example of the hair transplantation, the tool may be operated to harvest or implant follicular units by substantially automatically changing a direction of travel of the tool based on the locations of the reference points or fiducials. Harvesting and implant sites may be selected based on one or more criteria, one of which may be to minimize interference from fluids on the body surface. Another such criteria may be selecting locations which do not comprise locations of previously harvested or implanted follicular units.

One embodiment of the method may comprise recording first locations of a plurality of fiducials, and updating and recording updated locations of at least one or more of the plurality of fiducials, for example, to account for movement, whether that be due to interruptions or merely patient movement. The method may further comprise determining an offset of the updated locations of at least some of the plurality of fiducials relative to the first locations and selecting a procedure site, such as a follicular unit harvesting or implanting site, based at least in part on the determined offset. In some embodiments, the locations from where follicular units are harvested or into which follicular units are implanted are recorded, and a visual representation of the harvested or implanted follicular unit may be created.

According to another aspect, a system is provided that may include a processor comprising a set of instructions for executing operations for moving a tool to perform a procedure, for example, moving a tool to a site where a procedure is to be performed. For example, with reference to hair transplantation procedure, a set of instructions may comprise instructions for selecting a procedure site from where follicular units are to be harvested (or where follicular units are to be implanted) based on first locations of the plurality of fiducials appearing in one or more images of the body surface; and updating and recording updated locations of at least one or more of the plurality of fiducials. The instructions may further provide for a boundary of an area on a body surface to be determined, the area from which follicular units can be harvested from or implanted into. The instructions may also provide for determining an offset of the updated locations from the first locations and selecting a procedure site, such as a follicular unit harvesting or implanting site based at least in part on the determined offset. The instructions may further comprise instructing a tool to move to the site and/or perform the procedure, such as harvest from a selected harvesting site or implant into a selected implant site, optionally, outside or within the determined boundary. The system may comprise an image acquisition device to provide image data containing one or more images of the body surface with fiducials thereon and an interface adapted to receive an image data containing images of a body surface. The system may further comprise a processor configured to create a virtual representation of the site where the procedure has been performed, a representation for example of any harvested or implanted follicular units, and a monitor configured to display the same.

The system and method of the present invention is especially useful when implemented on, or integrated with, an automated system, for example, a robotic system comprising a robotic arm.

According to another aspect, a system and a method for controlling a direction of travel of a tool relative to a body surface is provided, in which the tool is caused to move or travel in an identified direction and operated to perform an action or procedure, for example, to harvest or implant follicular units in the direction of travel. The direction of travel or, in some embodiments also a boundary, may be determined, for example, based on a plurality of fiducials, which may comprise a set of distinctive fiducials. In some embodiments, the tool is operated to travel in a direction other than the direction of travel when another fiducial is within a predetermined distance from the tool. The direction other than the direction of travel may be substantially opposite the direction of travel or may be substantially orthogonal to the direction of travel. A change of direction of travel may be substantially automated based, for example, at least in part on the location of the fiducials.

According to yet another aspect, a system and method of operating a tool to harvest or implant hair grafts is provided, in which at least one image of a body surface is processed to divide the image into multiple rows and a tool may be operated to harvest or implant at least one follicular unit in a first row. A determination may be made whether a number of harvested or implanted follicular units in the first row is within a range of a desired number of harvested or implanted follicular units for the first row. If the number of harvested or implanted follicular units in the first row is within the range of the desired number of harvested or implanted follicular units for the first row, the tool may be moved to a subsequent row. However, if the number of harvested or implanted follicular units in the first row is less than a lower threshold value of the range of the desired number of harvested or implanted follicular units for the first row, harvesting or implanting the at least one additional follicular unit in the first row may be continued.

According to still another aspect, a system and method of operating a tool to harvest or implant hair grafts is provided, in which one or more images of a body surface are processed to determine locations of a plurality of distinctive fiducials appearing in the one or more images. The one or more images may be divided into multiple rows and a tool may be operated to harvest or implant at least one follicular unit in a first row at a first location. A direction of travel of the tool relative to a body surface may be identified based on the first location and the locations of at least some of the plurality of distinctive fiducials. The tool may be caused to travel in the identified direction of travel. A determination may be made whether a number of harvested or implanted follicular units in the first row is within a range of a desired number of harvested or implanted follicular units for the first row. If the number of harvested or implanted follicular units in the first row is within the range of the desired number of harvested or implanted follicular units for the first row, the tool may be moved to a subsequent row. However, if the number of harvested or implanted follicular units in the first row is less than a lower threshold value of the range of the desired number of harvested or implanted follicular units for the first row, harvesting or implanting the at least one additional follicular unit in the first row may be continued. The tool may then be operated to harvest or implant a second follicular unit at a second location on the body surface in the direction of travel.

According to a further aspect, a processor is provided comprising a set of instructions for executing operations, the set of instructions including instructions for processing one or more images of a body surface to determine locations of a plurality of distinctive references appearing in the one or more images; operating a tool to perform a procedure or operation, for example, to harvest or implant a first follicular unit, at a first location; identifying a direction of travel of the tool relative to a body surface based on the first location and on the locations of at least one of the plurality of the distinctive references; causing the tool to travel in the identified direction of travel; and operating the tool to perform an action or operation, for example, to harvest or implant a second follicular unit, at a second location on the body surface in the direction of travel. The instructions may further comprise utilizing at least one of the plurality of distinctive references to define a boundary, and operating the tool to perform the procedure or operation within the boundary.

According to yet another aspect, a method for defining a region of operation of a tool during a procedure or operation, for example hair transplantation, is provided. The method may comprise selecting a fiducial in an image of the body surface and moving, for example, an image acquisition device such that the fiducial is substantially at a reference point in the field of view of the camera. A location of the fiducial is determined in a frame of reference of the body surface. A subsequent fiducial may be selected, the subsequent fiducial being a closest to the fiducial for which the location has been identified. The method further comprises moving the image acquisition device such that the subsequent fiducial is substantially at the reference point in the field of view of the camera and determining a location of the subsequent fiducial with respect to the initial fiducial. The steps of selecting the subsequent fiducial and determining the location of the subsequent fiducial may be substantially automatically repeated for a set of fiducials that define a boundary of an area for performing a procedure or operation, for example for harvesting or implanting follicular unit.

According to a further aspect, a system and method for defining an exclusion region or zone is provided and information about the exclusion region is used in determining the next procedure or operation location, for example, for determining the next harvesting or implantation location. The exclusion region is the region within which is not desirable to perform a procedure or operation, for example, the region from which harvesting follicular units or into which implantation of the follicular units is not desirable. In some embodiments, the exclusion zone may be defined as a closed polygon, for example, a polygon of substantially tear-drop shape on a surface of the body, or for example a donor area, such as scalp.

In various aspects, systems and methods may be provided that further enhance a selection of follicular unit harvesting or implanting sites. In various cases, such selection may be made using, for example, a lowest and closest method, overlap-based methods, position-based methods, pattern-based methods (for example, a triangular pattern based method), and/or a combination of these methods. In various combinations of the methods, the output selection from one of the methods may be used as an input for one of the other methods to select one of the best candidate sites.

Other and further objects and advantages of the invention will become apparent from the following detailed description when read in view of the accompanying figures.

BRIEF DESCRIPTION OF THE DRAWINGS

It should be noted that the drawings are not to scale and are intended only as an aid in conjunction with the explanations in the following detailed description. In the drawings, identical reference numbers identify similar elements or acts. The sizes and relative positions of elements in the drawings are not necessarily drawn to scale. For example, the shapes of various elements and angles are not drawn to scale, and some of these elements are arbitrarily enlarged and positioned to improve drawing legibility. Further, the particular shapes of the elements as drawn, are not intended to convey any information regarding the actual shape of the particular elements, and have been solely selected for ease of recognition in the drawings. Features and advantages of the present invention will become appreciated as the same become better understood with reference to the specification, claims, and appended drawings wherein:

DETAILED DESCRIPTION OF THE PREFERRED EMBODIMENTS

Figure 1:
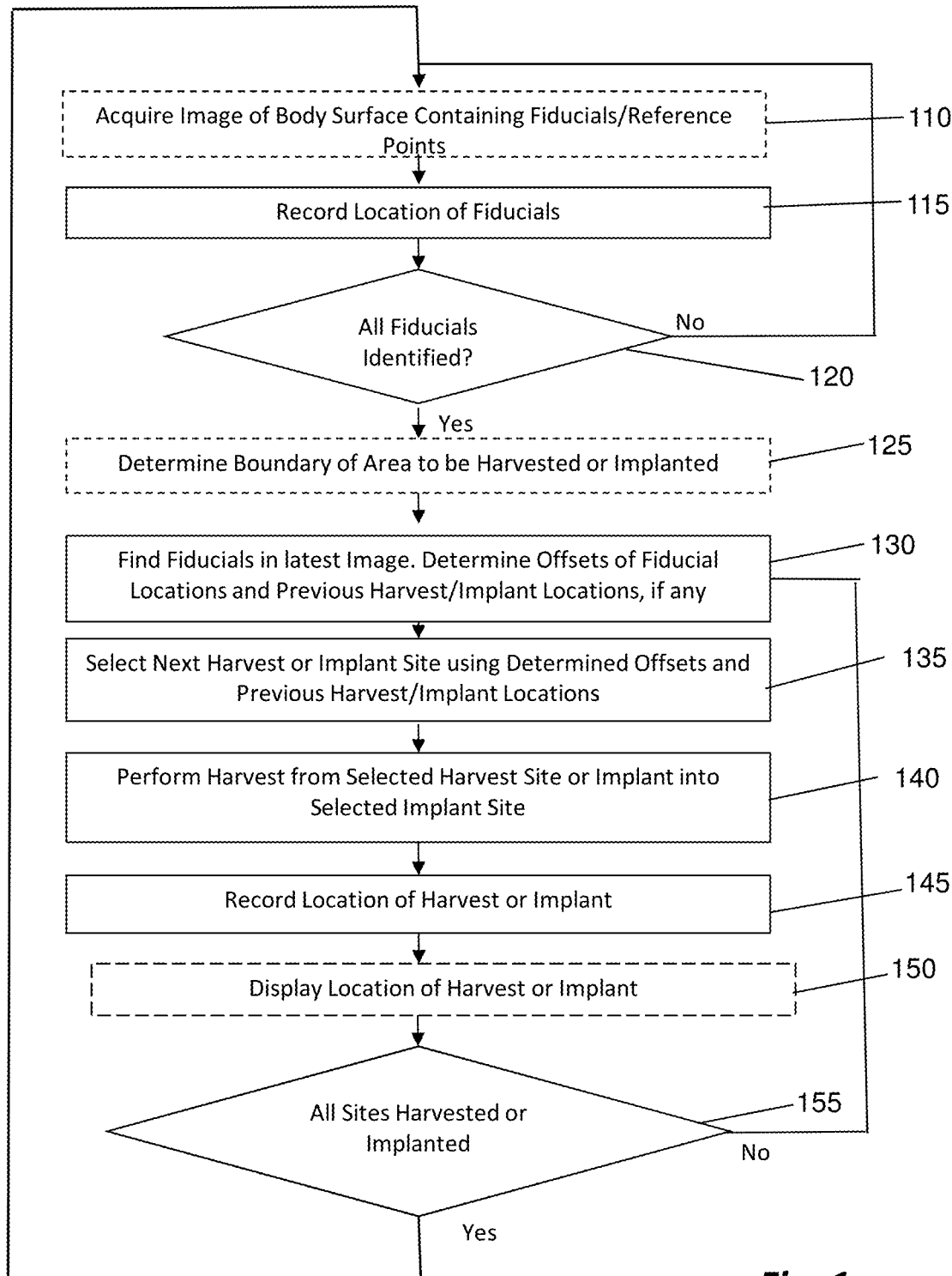
FIG. 1 is a block diagram illustrating a general methodology of an example of an embodiment according to one aspect of the invention.

In the following Detailed Description, reference is made to the accompanying drawings that show by way of illustration some examples of embodiments in which the invention may be practiced. In this regard, directional terminology, such as "right", "left", "upwards", "downwards", "vertical", "horizontal" etc., are used with reference to the orientation of the Figure(s) being described. Because components or embodiments of the present invention can be positioned or operated in a number of different orientations, the directional terminology is used for purposes of illustration and is in no way limiting. It is to be understood that other embodiments may be utilized and structural or logical changes may be made without departing from the scope of the present invention. The following description, therefore, is not to be taken in a limiting sense, and the scope of the present invention is defined by the appended claims.

The term "tool", as used herein refers to any number of tools or end effectors that are capable of performing an action, procedure or operation in various medical procedures or applications. For example, the tool may be a needle, a surgical scalpel, blades, various types of forceps, hemostats, surgical instruments, retractors, electrosurgical tools, radio-frequency ablation tools, suturing devices, tattoo placement or removal tools, eye speculum, cannula, drills or lasers. With reference to hair transplantation procedures, a "tool" may comprise a "harvesting tool" or an "implantation tool", and is capable of dissecting, harvesting or implanting follicular units ("FUs") from or into a skin or body surface, for example, a scalp. Such tools may have many different forms and configurations. In many embodiments, the tool comprises a hollow tubular shaft and thus may be labeled, for example, a cannula, a needle, or a punch. The distal end of such tools (for example, punches, coring devices, cutting and/or trimming devices, needles), are typically sharpened, to various degrees, to penetrate tissue and extract or implant the follicular unit. The terms "operatively connected," "coupled," or "mounted," or "attached" as used herein, means directly or indirectly coupled, attached, or mounted through one or more intervening components.

Embodiments of the methods of the present invention may be implemented using computer software, firmware or hardware. Various programming languages and operating systems may be used to implement the present invention.

Hair transplantation procedures that are carried out using automated (including robotic) systems or computer-controlled systems have been described, for example, in the Publication No. US 2007/0106306 commonly owned by the assignee of the present application, which is incorporated herein by reference. Robotics systems, such as robotic hair transplantation systems generally require accurate positioning of a tool under robotic control. When implementing a semi-automated or a fully automated procedure that requires precise control of the position, such as hair transplantation, it is desirable to be able to maintain such precise control despite patient motion or temporary interruptions. According to one aspect disclosed herein, the present application provides methodology for negating the effects of patient's movement or procedure interruptions. For example, the described methodology avoids further delays related to repositioning of a patient relative to a robot or an automated tool, and/or need for potential recalibration or a new treatment plan to be configured.

According to the various embodiments described herein, a variety of methodologies and systems are provided which enable a tool to automatically proceed from where it left off prior to an interruption that the procedure may be subject to, continuing its operation and essentially providing a seamless operational procedure. The systems and methods described herein enable the tool to maintain its direction of travel over the patient's body surface that it had despite patient's movement or other interruptions, to recognize where it has previously harvested follicular units or implanted them, and continue to travel in that general direction to harvest or implant further follicular units. The inventions described herein enable the system to operate in a fully-automated fashion, if desired, without requiring relocation of the base of the robotic system, relocation of the body surface, physician assistance or human intervention. In addition, the present invention provides methodologies that enable a tool operated by an automated system or under computer control to be operated to change its direction of travel when required, without necessarily requiring human intervention, although a user could overwrite any automated movement if desired.

Although the various examples and embodiments described herein will use follicular units (naturally occurring aggregates of 1 to 4 hair follicles) or hair grafts for purposes of describing the various aspect of the invention, it should be apparent that the general understanding of the various concepts discussed can be applied more broadly to other appropriate applications. It should be understood that although the methods described herein are especially suited for use with a robotic system for hair harvesting and/or implanting, they can be applied to other automated and/or computer-implemented applications. For example, devices, systems and methods described herein may be utilized in various ablation procedures (e.g. radiation-based), biopsy procedures, spinal procedures, dermatological procedures (e.g., tattooing or tattoo removals, ophthalmic procedures, or treating various dermatological conditions, such as skin cancers). It should be noted that the examples given herein are for the purposes of illustration and example only, the description as set forth is not intended to be exhaustive or limiting.

FIG. 1 is a block diagram illustrating an example of a general methodology employed by the present invention. At step 110 (which may be a preliminary step and it is shown in dotted line), one or more images of the body surface with one or more reference points, such as a plurality of fiducials, may be obtained, for example, using an image acquisition device. That may be accomplished by any technique known in the art. For example, in some embodiments an image acquisition device may be attached to a robotic arm, and the robotic arm with the attached image acquisition device may be positioned so that the harvesting or implantation region is in focus for the cameras. In other embodiments, the image acquisition device may be still incorporated into the automated (e.g., robotic) system but it does not have to be attached to the robotic arm. Alternatively, in further embodiments, the image acquisition device could be a device separate from the robotic system. As used in this application, a fiducial is an object that may act as a reference, and may be identifiable in a field of view of an imaging device. Fiducials can take many forms, for example, a single artificial reference point that uniquely identifies both position and orientation may be used as a fiducial. Take for example, a set of coordinate axes printed on a surface. The origin, together with the directions of the X and Y axes, can uniquely identify the surface position and orientation. In another example, a set of artificial reference points that each uniquely specify a position can be used as fiducials. The combination of three or more such reference points can specify a unique frame of reference specifying both position and orientation. An example would be spheres with different colors. One sphere uniquely specifies a position in space, but not orientation. Two more spheres can be used to specify both position and orientation. In yet another example, natural features of a surface that have unique, recognizable patterns may be used as fiducials.

With reference to hair harvesting or hair transplantation or other procedures that could be performed on a body surface (including various layers of skin, face and its various parts, such as eyes, nose, eyebrows, etc.), natural physical features or anatomical landmarks present on the skin or other body surface that have unique, recognizable patterns (e.g., follicular units or hairs, moles, scars, freckles, wrinkles, bumps or depressions on the body surface, eye balls, ear canals) may be used as fiducials. In the case of natural physical features or anatomical landmarks, these may be distinctive from one another based on their distinctive physical attributes (including but not limited to size, color, shape, number, height from the body surface etc.) or their relative distance from another distinctive feature. For example, working on the surface of a head, the random dot pattern of the entry locations of hairs on the surface of the head is sufficiently unique that a group of them can be used to unambiguously identify position and/or orientation. A pattern-matching algorithm can be used to recognize the hair pattern in subsequent images. In some embodiments, the fiducials may also be objects placed on or affixed to the patient's skin, sometimes called external fiducials. In the embodiments where external fiducials are used, they may be placed or affixed either directly to the skin surface in the hair donor or hair recipient area, or alternatively they may be placed on some device or instrument which is in turn affixed to the body, for example, a skin tensioner used in the hair transplantation procedures, as explained in more details in reference to the examples of FIGS. 3 and 4.

At step 115, a processor or an image processor, an example of which is described later in reference to FIG. 2, processes and records an identity and a location of each of the fiducials in a frame of reference of an image acquisition device (e.g., in a camera field of view). Such initial recording of fiducials could be referred to as "fiducial registration." The fiducials could be recorded in various coordinate systems, for example, in a fixed "world" coordinate system. In the example of FIGS. 4(a)-4(f), the fiducials are described as recorded in a coordinate system fixed to the camera. In situations in which an image acquired by the image acquisition device includes only a subset of the fiducials such that images of additional fiducials are needed, step 120 provides for acquiring additional images as needed, for example, including other subsets of the fiducials, until all fiducials have been identified. (This aspect will be described in greater detail with respect to FIG. 5). In an optional step 125 (shown in dotted line), based on the location of the each of the plurality of fiducials, a boundary of an area, such an area within which hair grafts or follicular units are intended to be harvested from or implanted into, may be determined. The boundaries may be determined automatically, for example, by drawing lines between various fiducials. The boundaries may be also adjusted to eliminate certain portions of the bound area where harvesting or implantation is difficult, as explained and described in further detail in reference to FIG.

3. In order to accommodate for patient motion, temporary interruptions, and any other incident that may cause a shift in location of the fiducials in the camera reference frame, as often as required (as may be determined by the user), updated images of the body surface are acquired, the images containing an image of the plurality of fiducials or a subset thereof. Due to patient motion, or another such temporary interruption, the locations of the fiducials in these updated images may be in a revised location with respect to the frame of reference of the image acquisition device. The processor in step 130 processes the revised location of each of the plurality of fiducials in the frame of reference of the image acquisition device, the revised locations of each of the plurality of fiducials which may be different from the locations previously processed. Having acquired the revised locations of the fiducials, and with the knowledge of the original locations of the fiducials, an offset for at least some or all of the fiducial locations may be determined in step 130. Based on this offset information, the processor also in step 130 may process revised locations for each of the locations of interest, such as locations from which follicular units have already been harvested (if harvesting has already started in a region of interest within the boundary) or into which follicular units have already been implanted (if such implanting has been started). Optionally, step 130 may also comprise determining the revised boundary, for example, of the harvesting/implanting area based on the revised locations of the fiducials. However, it is not necessary in some embodiments to determine the whole revised boundary as this information may be automatically ascertained simply based on the offset of the minimum number of the fiducials. In reference to the example of hair transplantation, having determined the offsets, and with the knowledge of the locations of the follicular units that have been harvested or implanted (if any) with respect of the fiducials, it is possible in step 135 to determine or select a location from where the next hair follicle is to be harvested such that hair follicles are not taken from an already harvested location, or determine a location into which the next hair follicle is to be implanted such that hair follicles are not implanted into locations into which hair follicles have already been implanted. Such selection may be made using a processor programmed to perform the above-described step, such as a processor described in reference to FIG. 2. In step 140, for example, a tool may be moved to the selected procedure site, and in some embodiments, the procedure may be performed at the selected procedure site: for example, a hair graft or follicular unit may be harvested from or implanted into the selected location. When the next hair follicle is harvested or implanted, the location from where it has been harvested from, or implanted into, may be registered or recorded by the processor in step 145. This registration may include information on the location of the harvest or implant with respect to at least one of the plurality of fiducials, or the determined boundary. Optionally, in step 150, the method may comprise creating and displaying a virtual representation on the image of the location from which the follicular unit has been harvested (or at least dissected from the surrounding tissue for further removal using forceps or vacuum), or the location into which a follicular unit has been implanted. Such visual representation, for example, on a monitor (e.g. a computer screen) is especially beneficial for the user to easily and quickly identify locations where hair grafts have been dissected or harvested, and also to differentiate between the previously existing follicular units and the newly implanted ones. The visual representations of step 150 may be implemented by using different colors, shapes or other appropriate differentiating features. In step 155 the processor determines, based on the information it has recorded with respect to the area and the locations of the follicular units that have been harvested or implanted, if follicular units have been harvested from all desired sites, or if follicular units have been implanted into all desired sites. In the event that all follicular units have been harvested or implanted, the processor may communicate this information, for example, to the image acquisition device. In addition, the processor may communicate this information to the user, typically providing an indication to the user (via the monitor, voice command, or any other appropriate technique), for example, that step 110 may begin again at a new donor or recipient region. In the event there are still follicular units to harvest or implant, the processor continues to repeat steps 130-155 until all desired follicular unit are harvested or implanted. For example, updated images with the updated fiducial information are processes, offsets determined, the next harvest site or implant site is selected, etc. In this manner, a methodology is provided to enable hair follicles to continue to be harvested from or implanted into a body surface in a continuous and automatic fashion despite potential patient movements and interruptions. The tool is able to be moved to each new harvesting or implantation location with respect to fiducials, the fiducials providing a mechanism of recognizing the location of the harvesting/implanting area on the body surface, despite movement of the patient, or the image acquisition device.

Figure 2:
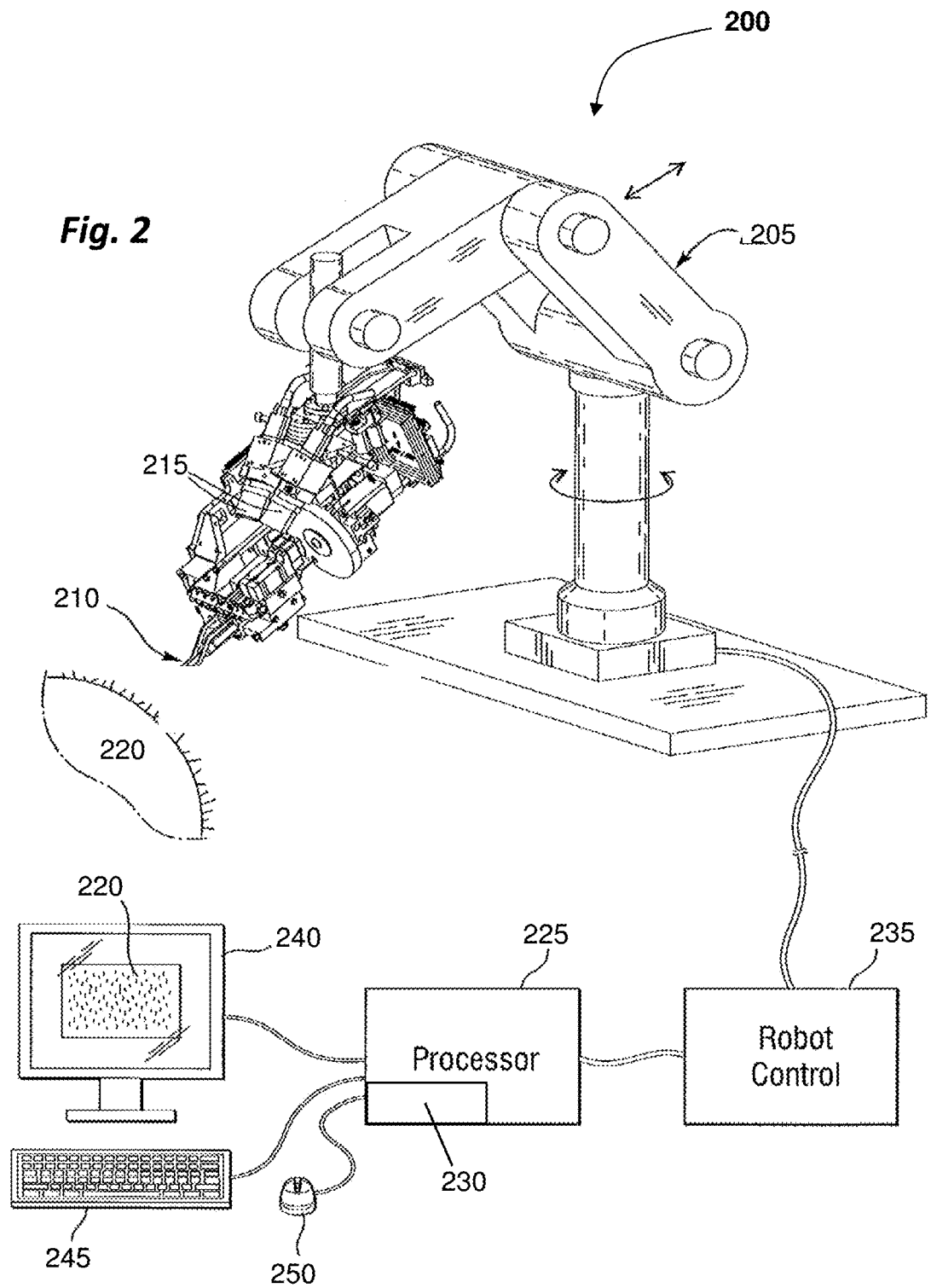
FIG. 2 is a schematic representation of an example of a robotic system that could be implemented in various embodiments of the invention.

Referring first to FIG. 2, an example of a system that may be used with the present invention is schematically shown. FIG. 2 is a schematic perspective view of an example of a robotic system 200 for hair harvesting (and/or implantation). The system 200 includes a robotic arm 205 to which is coupled a tool 210. Various motors and other movement devices may be incorporated to enable fine movements of an operating tip of the tool 210 in multiple directions. The robotic system 200 further includes at least one image acquisition device 215, which is described in more detail below. The image acquisition device may be mounted in a fixed position, or it may be coupled (directly or indirectly) to a robotic arm 205 or other controllable motion device. The operating tip of the tool 210 is shown positioned over a body surface 220, in this case a part of the patient scalp having hair follicles thereon. In some embodiments, an image acquisition device may be provided separately and not included in the system. In those embodiments, an interface may be provided that allows various other components or modules of the system, such as image processing component, to interact with the separate image acquisition device.

A processor 225 of FIG. 2, may comprise an image processor 230 for processing images obtained from the image acquisition device 215. The image processor 230 may be a separate device or it may be incorporated as a part of the processor 225. The processor 225 may also instruct the various movement devices of the robotic arm 205, including the tool 210 that may be operatively connected to the robotic arm. The processor 225 may act, for example, through a controller 235 as schematically shown in FIG. 2. The controller 235 may be operatively coupled to the robotic arm and configured to control the motion of the robotic arm, including the motion based on the images or data acquired by the image acquisition device. Alternatively, controller 235 may be incorporated as a part of the processor 225, so that all processing and controls of all movements of all the tools, the robotic arm and any other moveable parts of the assembly, including those based on the images or data acquired by the image acquisition device, are concentrated in one place. The system 200 may further comprise a monitor 240, keyboard 245, and mouse 250. A magnified image of the body surface 220 can be seen on the monitor 240. In addition, the system 200 may comprise other tools, devices and components, for example, those useful in harvesting, and/or implantation of the hair follicles, or in hair treatment planning. The system further comprises an interface adapted to receive an image data, various parts of the system allow an operator to monitor conditions and provide instructions, as needed. The processor 225 may interact with the imaging device 215 via the interface (not shown). The interface may include hardware ports, cables, leads, and other data transmission means, or it may comprise a computer program.

Some non-limiting examples of an image acquisition device 215 shown in FIG. 2 include one or more cameras, such as any commercially available cameras. Of course, various image capture devices (or imaging devices) could be used with any of the embodiments of the systems and methods described herein. For example, the imaging device may be one or more cameras, such as any commercially available cameras. While stereo or multi-view imaging devices are very useful in the present invention, it is not necessary to employ such geometries or configurations, and the present invention is not so limited. Likewise, although it is preferred that the image acquisition device be a digital device, it is not necessary. For example, the image acquisition device could be an analog TV camera that acquires an initial image which is then processed into a digital image (for example, via an analog-to-digital device like a commercial-off-the-shelf frame grabber) for further use in the method of the present invention. The image acquisition device may be coupled to a processing system, shown incorporated in the processor 225 in FIG. 2, to control the imaging operation and process image data. The processor for use in the present invention may comprise any suitable device programmed and configured to perform various methods described in detail in the present application, including methods directed to automated movement of the hair harvesting/implantation tool to maintain or change a desired direction of travel within a hair donor or hair recipient area; or methods directed in reference to FIGS. 4-7. For example, the processor for use in the present invention may be a processor comprising a set of instructions for executing operations, the set of instructions including instructions for processing one or more images of a body surface to determine locations of a plurality of distinctive fiducials appearing in the one or more images, (in some embodiments, the plurality of the distinctive fiducials may define a boundary); moving the tool to, and operating a tool to harvest or implant a first follicular unit at a first location; identifying a direction of travel of the tool relative to a body surface based on the first location and on the locations of at least one of the plurality of the distinctive fiducials; causing the tool to travel in the identified direction of travel; and operating the tool to harvest or implant a second follicular unit at a second location on the body surface in the direction of travel. It will be understood by those of ordinary skill in the art that the image processor for use with the present invention is programmed and configured to perform various known image processing techniques, for example, segmentation, edge detection, object recognition and selection. These techniques are generally known and do not need to be separately described here.

By way of example, and not limitation, a suitable processor or image processor may be a digital processing system which includes one or more processors or other type of device. For example, a processor (image processor) may be a controller or any type of personal computer ("PC"). Alternatively, the processor (image processor) may comprise an Application Specific Integrated Circuit (ASIC) or Field Programmable Gate Array (FPGA). The processor may also include memory, storage devices, and other components generally known in the art and, therefore, they do not need to be described in detail here. The above-described processor could be used in conjunction with various partially automated and fully automated (including robotic) hair transplantation and treatment systems and devices, including but not limited to systems for hair harvesting, or hair transplantation.

Figure 3:
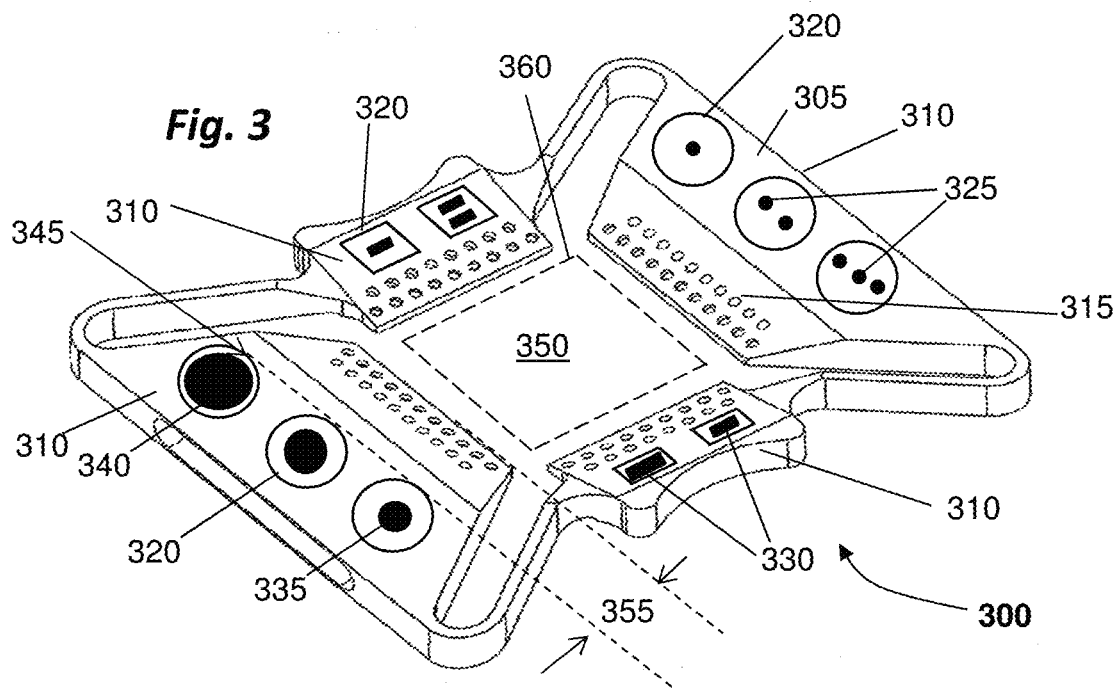
FIG. 3 is an example of a skin tensioner including fiducials which could be utilized in various embodiments of the invention.

In order to better understand how the method of FIG. 1 can be implemented utilizing a system such as that illustrated in FIG. 2, an example of arrangement of external fiducials is described in reference to FIG. 3. While performing hair harvesting, especially when using an automated system, such as a robotic system, it is often desirable to stretch the skin around the area of location of the follicular unit to be harvested. This could be done using a skin tensioner device. FIG. 3 illustrates an example in which a set of unique or distinctive (meaning that they are distinguishable or different from each other) fiducials are either formed on or affixed to a frame of a skin tensioner 300 that could be used in the hair transplant procedure to tension a skin surface from which hair follicles are harvested. Such skin tensioner could also be used in some embodiments during hair implantation if tensioning the skin surface is desired, in other embodiments fiducials could be placed directly on the skin surface during hair graft implantation. Moreover, in some embodiments natural features (e.g., moles, scars, etc.) could be used as fiducials. While the following discussion of the fiducials and their use will be described in reference to FIG. 3 and the skin tensioner, people of ordinary skill in the art would understand that this description may be adjusted and it is intended that the same principles should be applied to the fiducials placed, for example, directly on the skin or on the device other than the skin tensioner, as well as to the natural fiducials previously identified (e.g., follicular units or other physical landmarks). Therefore, such alternative implementations are within the scope of the invention. The skin tensioner 300 may comprise a flexible frame 305 that lies generally in a plane and shown to comprise a single element, typically molded material and is configured such that it may be compressed inward from a relaxed position. The flexible frame 305, in the example illustrated, includes four side sections 310. The four side sections 310 are shown linear and arranged substantially in a square, although they may be arcuate and otherwise arranged in various geometrical patterns. Each side section 310 features a plurality of perforations 315 for receiving barbs or microbarbs (not shown), which are small elements that project from skin tensioner to the skin below to puncture or form a depression in the skin surface, serving as a primary means of ensuring good grip between the skin tensioner and the skin. The illustrated fiducials 320 may comprise, for example, a set of circular fiducials 325, each circular fiducial 325 being distinguishable from any other circular fiducial, and a set of square fiducials 330, each square fiducial 330 being distinguishable from any other square fiducial. For example, as illustrated, the fiducials may comprise a single feature, for example a dot, and each fiducial may be distinguishable from the others by the size of the feature (e.g., the dot). Alternatively the fiducials may comprise a feature (such as a dot) that may be of the same (or different) size on each fiducial, but the fiducials may be further distinguishable from the one another, for example, by the number of the features (such as dots) that it has on it. In further alternative embodiments, each fiducial may comprise a different feature or features. The fiducials 320 can be of any shape or configuration, provided the imaging system is capable of distinguishing one fiducial from another. In the illustrated embodiment the imaging recognition software could, for example, recognize whether the fiducial it had identified was a circular fiducial 325 or a square fiducial 330 by determining the ratio of the square of the perimeter of the fiducial to the area of the fiducial. For example, this ratio for a circular fiducial 325 is around 12.5, and that for a square fiducial 330 is 16. Hence, having made this determination, the processor containing image processing software would be able to distinguish the set of 6 circular fiducials 325 from the set of 4 square fiducials 330, illustrated as an example in FIG. 3. In addition, a similar capability in image processing could enable the processor to determine that the ratio of the area of the single smaller dot 335 on the circular fiducial 325 to the area of the circular fiducial itself, was smaller than the ratio of a larger single dot 340 on the circular fiducial 325. Hence uniquely identifiable fiducials 320, such as those illustrated by example in FIG. 3, could be used to implement the methods of the present application. The fiducials 320 may be placed at a known distance away from the inner edges that form a central opening 350 of the skin tensioner. In the example of FIG. 3, this known distance is illustrated as a distance 355 and it is shown as a distance from an inner edge of the tensioner to a point 345 on a fiducial where the point 345 is the closest to the central opening 350 of the skin tensioner 320. Alternatively, a distance 355 may be measured from the inner edge of the skin tensioner to a center of the relevant fiducial. For example, in some embodiments the row of fiducials is placed such that the distance 355 may range between 1 mm and 10 mm (and in some embodiments may further range between 2 mm and 4 mm) from the inner edges of the tensioning device 300. In other embodiments, depending on the application, this distance 355 may have widely different ranges. Fiducials may be used to bound an area, for example, for harvesting, and may need to have a known relationship to that area. The processor may comprise an algorithm which detects the fiducials on each side of the skin tensioner (or on the skin or other alternative surface), fits lines to the four (in the example of FIG. 3) rows of fiducials and computes a quadrilateral whose corners are formed by the intersection of the best-fit plane containing all fiducials with planes passing through each line and normal to the all-fiducial plane. Based on the above and on the known distance from the near edge of the skin tensioner to the fiducials, the processor is consequently able to identify and calculate the area or central opening 350 bounded by the four side sections of the skin tensioner, which could represent the area within which it is desired that hair follicles be harvested from (or implanted into).

Utilization of a skin tensioner 300 to host the fiducials 320, may require other factors be taken into consideration when identifying the actual bound area where follicular units will be harvested or implanted. One such factor is that the skin tensioner itself has a depth or height associated with it, that is, it does not typically lie flush with the patient's body surface, but is raised above the body surface to a certain degree. It will also be appreciated that the angle at which the follicular units extend from the patient's body surface varies. To this end, there may be situations in which although there may be a follicular unit that is close to the inner edges of the skin tensioner 300, due to the depth/height of the skin tensioner and/or the angle at which the follicular unit emerges from the skin, the tool that will be placed inside the central opening 350 of the tensioner may not be able to be oriented properly relative to the follicular unit without interfering with the inner edges of the tensioner that define the opening 350. Therefore, a successful harvesting of the follicular unit could not be attempted. For this reason, in addition to using the information of a known distance from the fiducials to the inner edges defining the central opening 350, the processor may be also configured to take into consideration, for example, a depth or height of the inner edge of the tensioner, and/or an angle and dimensions of the tool/punch when it orients relative to a hair graft to harvest it (or relative to a desired orientation of the hair graft to be implanted). When these distances, angles and other relevant parameters are taken into account, the processor may determine, using a straightforward trigonometric calculation, a revised boundary 360. This revised boundary 360 provides a predetermined distance from the fiducials that the tool may safely approach, without encountering the physical inner boundaries of the tensioning device itself, encountering issues arising from one or both of the depth/height associated with the tensioning device, encountering image processing issues arising from the shadow cast by the tensioning device on the body surface, and/or the angle of approach of the tool. Alternatively, a calculation may be performed on each hair in the field of view in order to allow selection of only those hairs that are reachable without such interference from the tensioning device or issues arising from inadequate tool dimensions. This selection may be done by a user based on user-specified criteria input via, for example, a keyboard, selected via the mouse, or selection may be provided by an automated algorithm, to harvest or implant the next follicular unit accordingly. Having considered and accounted for all these variations, the location of the fiducials can be used to calculate whether the hair harvesting or implantation tool will clear the tensioner during the transplantation procedure.

Additional input criteria relating to the parameters of the procedure may also be selected at this time, allowing for automation of the procedure. Similar to that described above, these parameters may be input via a keyboard or a remote input device, or selected via the mouse, or selection may be provided by drop-down menus of an automated algorithm or similar such means. In this manner, the user may select, in reference to hair harvesting or implantation, for example, that the minimum distance from any previous harvest site be at least 2.0 mm, the minimum distance from a previously skipped harvest site be, for example, at least 0.5 mm, similarly, tensioner offset distance from each side may be selected as well, or the type of follicular unit to be harvested (F2, F3, or F4, for example), or any other such parameter(s). With respect to other procedures, the appropriate parameters for such specific procedure may be selected in a similar manner. For example, in a laser tattoo removal application, the user may select the angle of the laser to the body surface and/or the distance of the laser with respect to the skin. If instead of a tensioner some other boundary setting device is used, various distances as described above (e.g., offset on each side, etc.) may be selected by the user.

The present invention utilizes of a set of identifying fiducials such as those described above, to facilitate automation of a robotic system, such as follicular unit harvesting or implanting system. In some embodiments one or more of the fiducials are distinguishable from others, in others, all of the fiducials are distinguishable from each other. The fiducials serve as objects, or reference marks in a field of view of an image acquisition device. These identifying fiducials when viewed in an image can be recognized in the image, and may be individually recognizable from each other in subsequent images. Fiducials may be physically identified by a 1-D bar code, a 2-D data matrix code, known markings such as alphanumeric characters, a series of dots, a series of bars, or any other type of unique identifier or custom scheme. As mentioned above, the perimeter-to-area ratio, the ratio of area of the internal features to the outside features, and the number of internal features may be combined to ensure that a unique identifier can be determined for each fiducial.

Figure 4A:
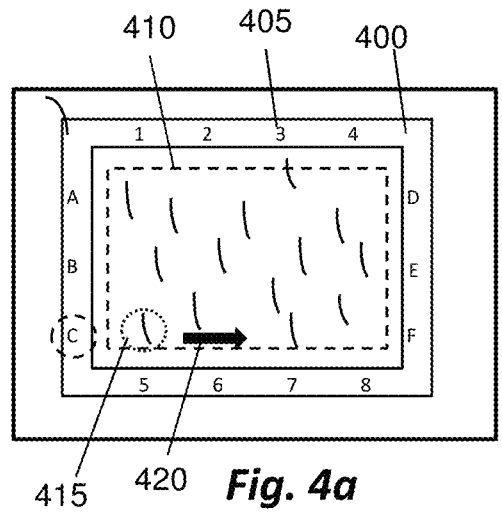
FIGS. 4(a)-(f) show various examples of implementations of the methodology according to an embodiment of the invention.

FIGS. 4(a)-4(f) illustrate how the steps of FIG. 1 can be implemented utilizing the system of FIG. 2 and fiducials, for example, similar to those as illustrated in FIG. 3. In FIG. 4(a), a tensioning device 400 is illustrated. In order to more easily explain the various methods of the current invention, rather than utilize fiducials such as those illustrated in FIG. 3, the discussion will utilize fiducials 405 which are illustrated as a series of alphabetic characters, A to F, along the vertical side sections of the skin tensioner, and a set of numeric characters, 1 to 8, along the horizontal side sections of the skin tensioner. The fiducials generally may be placed in arbitrary positions relative to a working area. As mentioned above, the fiducials are placed such that a known feature of the fiducial, for example the center of each fiducial, or a known boundary of the fiducial is at a known distance from inner bounding edge of the skin tensioner. For example, the fiducials may comprise circular shaped adhesive labels that affix to the tensioning device, the edges of the circular shaped adhesive labels being such that the size of the label is less than the size of the vertical and horizontal structures of the tensioning device to which it is attached, so that when placed on the tensioning device, the fiducials themselves may be located, for example, in the region of 2 mm or so from the inner boundary of the tensioning device. It is desirable to position fiducials (whether it is on the tensioner, or on a skin itself) or locate natural fiducials, such as follicular units, such that the relative position of the fiducials do not change, or if they do, they do not change significantly during the procedure. The system, in particular the processor, can process images acquired by the image acquisition device to detect substantial relative motion, for example motion in the region of 1 mm in a field of view in the region of 50 mm, that may be caused, for example, by misidentification or detachment of a fiducial (if it is an externally placed fiducial), and report such an error so that measures may be taken if necessary to compensate or correct for the error. Of course, the surface on which the fiducials are located is free to move (e.g. patient moving his/her head or getting up). The translation and rotation of the surface with the fiducials due to motions can be computed any time when at least three non-collinear fiducials are visible. When the shifted and/or rotated fiducial locations are detected (for example, by an imaging device and/or image processing software or hardware which may form a part of an imaging system), the procedure is able to continue at the next harvest site. If fewer than three non-collinear fiducials are visible, another attempt to image and register fiducials is made so that three or more fiducials become visible, as described in more detail in reference to FIGS. 5(a)-5(g).

According to the methodology of an embodiment of the invention, and with reference to FIG. 4(a) the location and optionally the orientation of each of the fiducials 405 may be identified, registered, and electronically saved via the image processor. In addition, the user may also specify via an input device such as the keyboard or the mouse, information pertaining to the physical parameters of the tensioning device 400 (if such tensioning device is used) and the tool, information such as the height of the tensioning device 400 relative to the body surface and the diameter of the tool for example. Based on this information, the processor may, optionally, determine the location and orientation of a revised boundary 410. To aid in the understanding, it will be assumed that the fiducials 405 are recorded in the coordinate system of the image acquisition device, which as indicated above is on the robotic arm, though they may be recorded in any appropriate reference frame.

Having registered the location and possibly the orientation (when applicable) of each of the fiducials 405, the image processor identifies the location and optionally the orientation, of one or more hair harvesting (or implantation) sites 415, and may register and electronically save such identified information. Optionally, if the revised boundary 410 has been determined, the image processor identifies the location and possibly the orientation of one or more hair harvesting (or implantation) sites 415 within the revised boundary 410. The information about location and orientation of the harvesting (or implantation) site is registered and stored with respect to the location and orientation of the fiducials 405. This enables monitoring and control, for example, of the spacing between hairs to avoid under harvesting (when harvest density is too low) and overharvesting (when harvest density is too high). Optimal density can be maintained only if the system, such as the robotic system is able to maintain its knowledge of the harvest (implant) area, and use the full area available for harvesting or implanting. When the fiducials are used to define the boundaries, for example, of the harvest area, harvesting may be automatically performed as close as desired to that boundary. The harvesting mechanism can turn automatically to start a new row when the boundary is approached, and can stop automatically when the full area bounded by the fiducials has been harvested. Automation of the hair harvesting (or hair implantation) procedure is facilitated by maintaining harvest direction and row-to-row spacing despite patient motion as discussed below.

FIGS. 4(a)-4(f) will be discussed, as an example, in reference to the hair harvesting, and assuming that revised boundaries 410 are utilized. However, it should be understood that this description applies and could be adjusted accordingly in reference to hair implantation, and to eliminate the determination of revised boundaries 410. As illustrated in FIG. 4(a) the harvesting tool is operated to initiate the harvesting procedure from the bottom left hand corner of the quadrilaterally shaped bound area, bounded by the revised boundary 410. During the hair transplantation process, often various fluids, including for example, blood and saline will be present on the body surface. It was discovered that it is advisable, especially in the computer-implemented or robotic hair transplantation procedures, that the harvesting or implantation process begin from the bottom of the frame, whether it be in the right or left corner. This way any appearing blood or other fluid will tend to flow downwards, and therefore, will less likely compromise the image of the potential subsequent hair harvesting or implantation sites, thus optimizing any image processing that may be implemented. The harvesting tool may be moved to the initial or first harvesting location, such as location 415 in FIG. 4(a), directly or indirectly by the physician (for example, the physician may click on the image to identify the desired harvesting location), or the processor may be configured or programmed to find this location itself, for example, based on the information it has acquired on the fiducials, the processor may then provide instructions to the control unit to move the tool accordingly.

In this particular instance, the tool has been instructed to move to the location approximately corresponding to the position C5, and the tool is operated to harvest a follicular unit at the harvesting site 415. In one embodiment according to the provided methodology, the processor may create a visual representation of the location on the site at which the follicular unit has been harvested This representation may comprise a circular shape such as that illustrated, a cross, or any other such visualization. The visual representation or the marking of the harvesting (or implantation) site is beneficial to the user of the system, providing a visual image of where harvests (or implantations) have occurred. Moreover, in some embodiments, it may be desirable to highlight the above-mentioned visual representation of the harvesting or implantation site in a distinctive color. The tool is then controlled to move in the direction represented by arrow 420, along the row defined by virtual line C-F, substantially parallel to a horizontal side of the revised boundary 410. Although for convenience, the drawings of this application show that follicular unit implantation or harvesting takes place in straight rows and columns, it should be apparent to those in the field that naturally grown follicular units do not grow in straight rows and columns, and needless to say it is not intended that the present invention be read is such a restrictive fashion. The column and row explanation has been used for ease of understanding only, and locations at any reference location fall within the scope of the application.

Figure 4B:
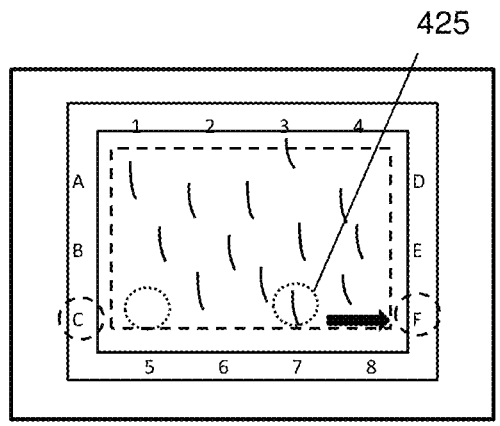
Figure 4C:
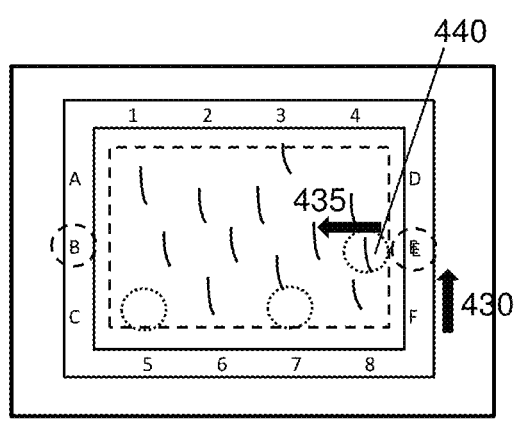

As indicated in FIG. 4(b) the processor can be configured to operate the tool to harvest follicular units at predetermined locations, such as in this example, by passing over, for example, any locations in row C-F between fiducial locations 5 and 7 without harvesting a follicular unit, and making its subsequent or second harvest at the location 425 that could be defined as C7. It should be understood that the selected harvesting location, for example, on the row C-F does not have to be exactly at the level of the location of the fiducials 405 (such as fiducial 7), but rather may be anywhere and at any distance from a particular fiducial (e.g., between the level of fiducials 6 and 7). When the processor determines that the tool is within a predetermined distance from fiducial F and the end of this first harvesting row, or that the revised boundary 410 has been reached, the processor provides instructions to the control unit to cause the tool to move in a direction away from fiducial F to automatically increment to the next harvesting row. In this particular case, as illustrated in FIG. 4(c), the tool is controlled such that it moves initially in an upwardly direction 430, from F to E, and then in a direction denoted by arrow 435, away from E, away from the revised boundary 410, and along the virtual line EB. In this case, the tool is controlled to move to a harvesting site 440 located at approximately B-8, and operated to harvest a follicular unit at that location before moving on. This procedure can continue without requiring intervention from the operator or physician. It should be understood, however, that the operator may intervene at any time to overwrite an automated movement and select a different follicular unit to be harvested, if desired or necessary. The system is configured to direct a tool to move and operate, for example, at least in part based on the location of the fiducials. In this manner, the tool can be operated to turn automatically when the revised boundary is approached and start the next row of the harvesting process, and to stop automatically when the area bound by the revised boundary 410 has had all desired follicular units harvested.

Figure 4D:
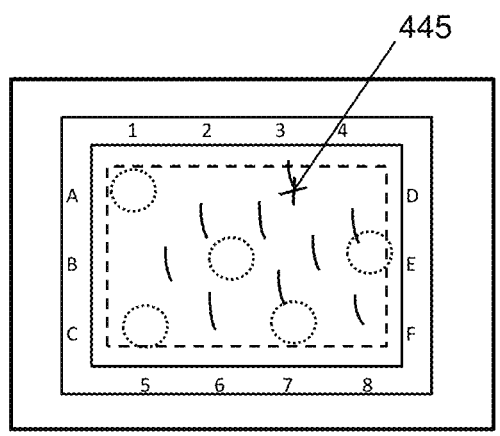
Figure 4E:
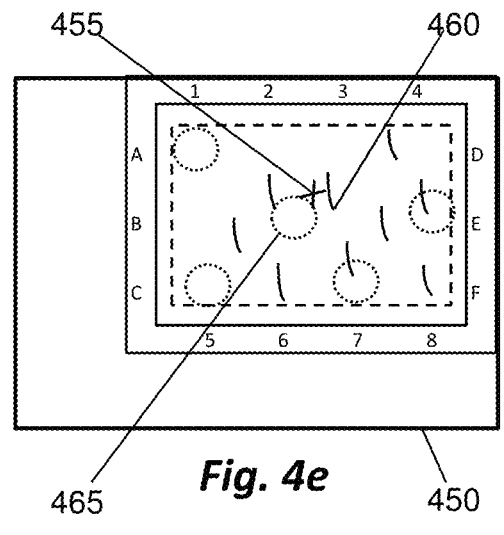
Figure 4F:
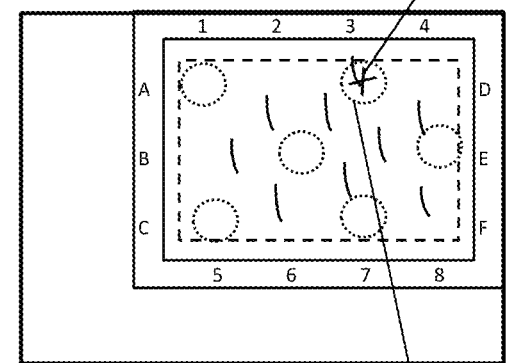

According to another example of implementation according to the inventions described herein, FIG. 4(d) indicates a location 445 denoted by an "X", at which it is intended that the next follicular unit be harvested. However, let us assume that for whatever reason, there is an interruption, perhaps the patient moves, either temporarily leaving the operation chair, or just shifting to get in a more comfortable position. Even though the patient has moved, the view seen by the camera which is in this instance located on the robotic arm, will be substantially unchanged in the global context, that is, the view relative to the chair will be the same (assuming that the chair is not moved with respect to the robot). However, the view with respect to the patient's body surface may be different. As indicated in FIG. 4(e), the patient's body surface may have moved such that the existing follicular units can be seen to have moved both to the right, and upwardly, in the frame of view 450. If the tool was moved to harvest the next follicular unit at a location with coordinates referenced with respect to the frame of view 450, it can be seen that the follicular unit would be harvested from a location 455 marked with the "X" which is not the original desired location marked as 445 in FIG. 4(d). As indicated in FIG. 4(e), this location 455 is close to another follicular unit 460 that could be damaged by harvesting the location 455. This location 455 is also close to a location from which another follicular unit has already been harvested, location 465. Moreover, this would not maintain the intended row-to-row spacing of harvested follicular units, and does not maintain the intended spacing of the harvested follicular units from one another. By registering the intended harvesting site with respect to the fiducials 405, the robotic system is able to avoid some or all of these errors, and additionally is able to continue the harvesting process without necessarily requiring significant intervention of the physician to do so. The robotic system is configured to determine the location and orientation of each of the fiducials 405, and compare these new or revised locations and orientations with the already saved information on each of the distinctive fiducials 405. For example, in this particular case, it will determine that the location of each of the fiducials 405 has moved a certain distance towards the right hand side of the frame of view, and a certain distance in an upwardly direction also. Using fiducial tracking techniques that are known in the art, the system is able to determine how each of the initially identified fiducials has been transformed in location and orientation, and determine the transformation that needs to be applied to the location 455, to relocate that same location 455 with respect to the fiducials 405. Having acquired this information, the processor is then able, using known transformation techniques, to modify the location and orientation information of the intended implantation location 455 accordingly, applying the necessary transformation of the coordinates of the location, so that the tool can be operated to move to the correct harvesting site 470 (which correspond to the originally marked site 445), as illustrated in FIG. 4(f). In this manner, the system is configured to operate the follicular unit harvesting tool to maintain its harvesting direction that is along the virtual row A-D, despite patient movement. In addition, the system is configured to ensure that harvesting does not occur at sites where harvesting has already taken place, enabling site to site spacing and row-to-row spacing to be maintained. To this end, the provision of visual image, for example, in the form of circles centered about where harvesting has been performed, provides the user with a visual representation that confirms that harvesting has occurred at the site to site spacing and row-to-row spacing desired. Obviously, should the visual circular representations not correspond with the desired outcome, the user has an opportunity, based on the recognition of the deviation from expectation, to correct for any errors that may be visualized. This correction can be implemented at any moment that deviation from expectation has been detected, and multiple corrections may be performed throughout any procedure. In this manner, the system is able to harvest follicular units despite patient movement. It will be appreciated that although the above has been described with respect to the harvesting process, the methodologies described above can be easily adapted to apply to the implantation process, or other procedures.

According to another aspect of this application, harvesting and implantation locations could be used to define "exclusion zones" around harvesting or implantation sites. For example, arbitrarily shaped features or structures may be utilized to facilitate selection of the next harvest or implant site, which may optionally be visually represented to the user. In one embodiment, the perimeter or an outline of the arbitrarily shaped feature can be tailored to indicate an exclusion zone, that is an area within which selection of the next potential harvesting site or a potential implantation site should be avoided. A more detailed discussion of the exclusion zone as used in the present application is provided below.

To aid with the understanding of the exclusion zone, consider first a situation in which no harvesting or implanting is allowed when the distance between the proposed site and any previous harvest site is less than a given radius, and the harvesting tool penetrates a body surface substantially orthogonal to the body surface. In this situation, a simple circle (representing a simple exclusion zone) may be utilized to facilitate selection of the subsequent hair harvesting or implantation site, by creating the perimeter around a new potential harvesting/implanting site. The perimeter of such circle will be larger than the potential harvesting/implanting site to provide for an exclusion zone around the harvesting/implanting site, that is an area in which the tool should avoid harvesting/implanting a subsequent follicular unit. For example, such harvesting/implanting should be avoided if, in addition to the potential harvesting/implantation site, there is also a location of already previously harvested/implanted site within the perimeter of the circle, or perhaps within a predetermined distance from the perimeter. The exclusion zone may be based on various criteria, including, for example, avoiding problems such as the potential harvest/implant site coinciding, intersecting with, or coming too close to an already existing harvest/implant site, or merely defining the minimum separation of follicular units that are to be harvested/implanted for medical or aesthetic reasons.

The above methodology works well if one assumes that the harvesting tool enters the body surface substantially orthogonal to the body surface. However, hairs do not generally grow orthogonal to the body surface, or at least the portion of the hair beneath body surface does not grow substantially orthogonal to the body surface. Therefore, it is more likely that a harvesting tool will be approaching a scalp at an angle. Assume that this angle is an acute angle. Due to the acute angle of the approach, and the velocity of approach, the tool (such as a harvesting punch) may tend to skive the skin, sliding a little further than perhaps originally intended, and enter the body surface slightly off-center from the intended harvesting site. As the punch enters the body surface, it is doing so at an angle, and therefore as it continues to penetrate into the body tissue, it also does so at an angle. As the harvesting tool penetrates the body surface, the distal end of the harvesting tool may not only enter the body surface at a location that differs from the intended entry point (the intended harvesting site), but the distal end of the harvesting tool may also reach a location beneath the body surface that differs in the horizontal direction from the original location of entry on the body surface. It is therefore possible that on so doing, the distal end of the harvesting tool may coincide or intersect with an already harvested site, or a site that has already been implanted into. In this particular situation, relying on a circular-shaped feature may cause an unintentional overlap with an existing harvesting or implantation location, and therefore, may create potential problems. For example, harvesting a follicular unit that is too close to a previous harvest site can cause the skin between the two harvests to tear, resulting in excessive bleeding and scarring.

It is therefore an aspect of this disclosure to provide for an exclusion zone that is tailored to accommodate at least one or more of various factors, for example, with reference to hair transplantation, a minimum distance between harvests, a minimum distance between implants, the diameter of the tool, the angle of approach of the tool, the direction and/or velocity of approach of the tool, or the depth of penetration of the tool. In reference to other medical procedures, an exclusion zone will be tailored to the factors appropriate for such procedures. Such an exclusion zone may comprise any closed polygon-shaped feature, be it oval, elliptically-shaped, tear-drop shaped, or any arbitrarily shaped feature configured to accommodate or take into consideration the examples of the factors mentioned above. The parameters of the exclusion zone (its size, shape, and location) provide information that can be utilized by the processor in the selection of the next harvesting or implantation site, to exclude harvesting or implanting into already harvested or implanted regions, or too close to such regions, whether those regions be at the skin surface or below it. It also provides a visual indication to the user that appropriate selections of harvesting or implantation sites are being made by the automated hair transplantation system.

According to one aspect, as an example, a method for defining an exclusion region of operation of a tool during hair transplantation is provided. The method may comprise providing processing instructions that can cause an exclusion zone to be created around a potential harvest/implant site, the exclusion zone may be based on at least one of or more of a minimum distance between harvests, a minimum distance between implants, the diameter of the tool, the angle of approach of the tool, the direction and/or velocity of approach of the tool, or the depth of penetration of the tool. The method further comprises determining existence of any previous harvest or implant site that may lie within the exclusion zone, in addition to the proposed harvest/implant site. If a previous harvest or implant site lies within the exclusion zone, the proposed harvest or implant site is skipped, it is not harvested/implanted and the processor may select another proposed harvest or implant site, and check again. This selection process may be continued until a site is selected that passes an exclusion zone test, for example, the test of having no previous harvest or implant sites within its exclusion zone.

Figure 4G:
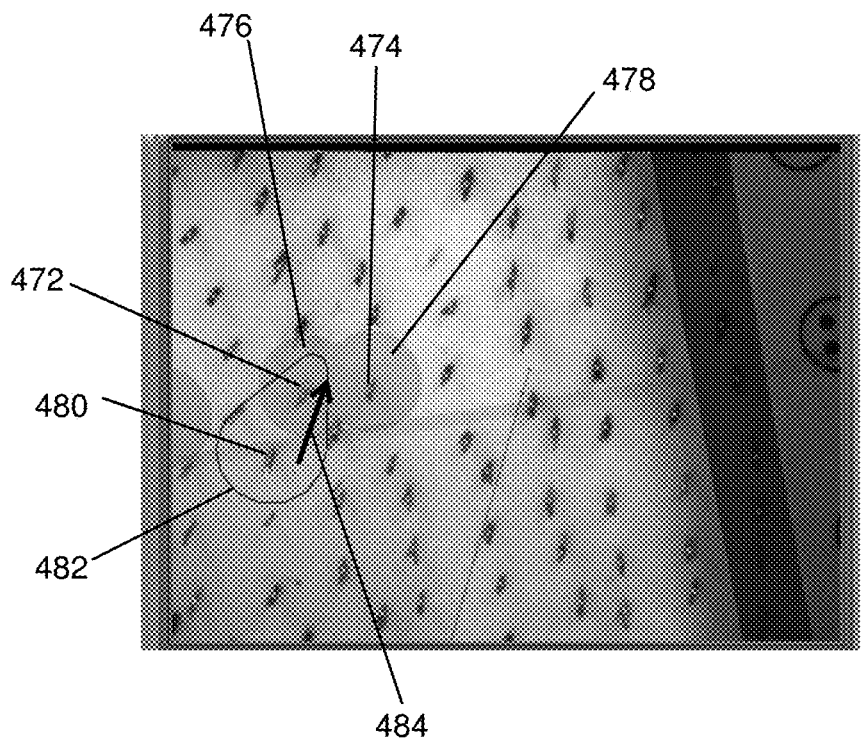
FIGS. 4(g)-(h) demonstrate an example of an embodiment according to "an exclusion zone" methodology.
Figure 4H:
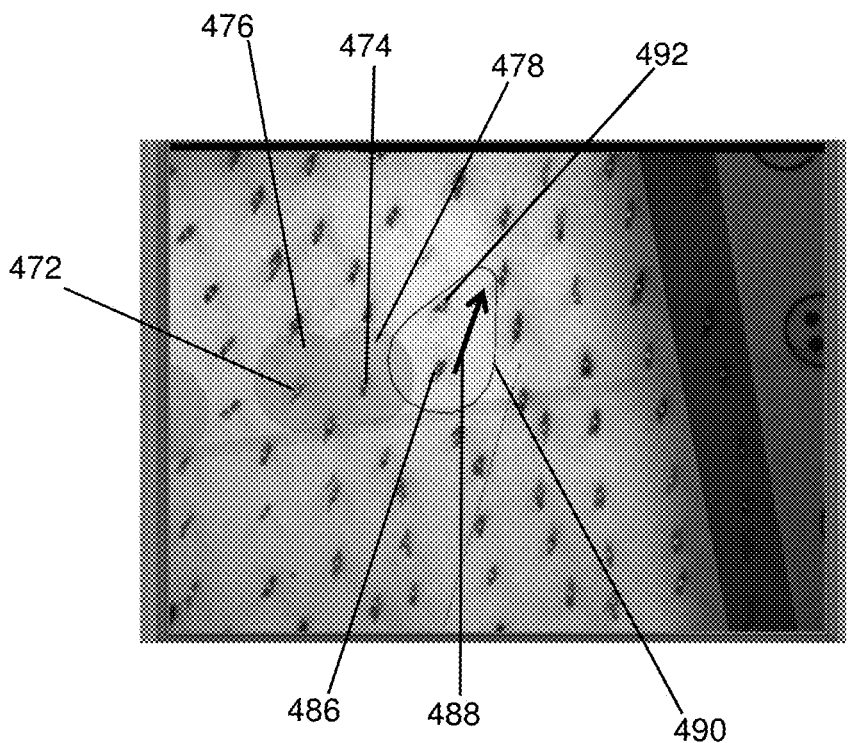

FIGS. 4(g) and 4(h) illustrate an example of an embodiment using an exclusion region methodology. Turning first to FIG. 4(g), already harvested locations 472 and 474 are identified with a circular representations 476 and 478 indicating larger regions centered about the harvest locations 472 and 474. These circular representations 476 and 478 provide a visual image of areas from which it is not desirable to harvest additional follicular units, as these would be too close to already harvested follicular units. The processor may select a potential harvesting location 480, which is outside the circular representations 476 and 478. In addition, the processor creates an arbitrary shaped feature 482, which in this instance is shaped as a tear-drop, around the potential harvesting location 480. As can be seen in the figure, the shape of the feature 482 can be described as a circle around the potential harvesting location 480, which has been extended, or stretched in the direction 484, which is the direction in which the tool is both travelling and angled to harvest, thus forming a tear-drop shape (or exclusion zone). Having created this exclusion zone 482, the processor determines whether there are any already harvested sites that fall within the exclusion zone 482 in addition to the potential harvesting site 480. In this instance, the already existing harvesting site 472 can be seen to fall within the exclusion zone of the tear-drop 482, and so the processor will determine that this potential harvesting site 480 is not a site from which a follicular unit should be harvested. Harvesting a follicular unit from this location 480, with the tool orientated at the selected angle and in the direction 484, could possibly create a harvesting path that coincides or intersects with the already existing path that was created at location 472. Therefore, the processor selects an alternative potential harvesting site, for example that indicated in FIG. 4(*h*).

In FIG. 4(*h*), once again already harvested locations 472 and 474 are identified with circular representations 476 and 478 indicating larger regions centered about the harvest locations 472 and 474, from which it is not desirable to harvest additional follicular units. The processor selects a potential harvesting location 486, which is outside the circular representations 476 and 478. In addition, the processor creates an arbitrary shaped feature 490 (or exclusion zone) which once again is shaped as a tear-drop, around the potential harvesting location 486. As can be seen in the figure, the shape of the feature 490 can be described as a circle around the potential harvesting location 486, which has been extended, or stretched in the direction 488, which is the direction in which the tool is both travelling and angled to harvest, thus forming a shape that is tear-drop shaped. Having created this exclusion zone 490, the processor determines whether there are any already harvested sites that fall within the exclusion zone 490 in addition to the potential harvesting site 486. In this instance, while there are follicular units within the exclusion zone 490, for example, the harvesting site 492, none of them has been harvested yet. Therefore, a candidate or potential harvesting site 486 is an acceptable candidate, and the processor may determine that this potential harvesting site 486 could be harvested without intersecting with any already existing harvesting path.

The generation of visual representations that define exclusion zones that are centered, for example, about a harvesting site, may create an image that has numerous overlapping representations, and consequently an image that has numerous gaps formed between each of the distinct exclusion zones. This is illustrated in FIG. 8(*a*) in which already existing procedure sites, such as harvesting sites 805, 810 and 815, each have associated exclusion zones 820, 825 and 830 respectively, created as described hereinbefore. The exclusion zones 820, 825 and 830 create a gap 835 as illustrated. Gaps such as these tend to create a rather "unfriendly" visual representation for the user and the processor. An image with a vast number of these gaps can make it difficult for the eye to easily identify or focus on the "larger" gaps, and may also consume additional processing time by the processor. By avoiding the creation of these gaps, and in particular the relatively small gaps, a visual representation that is more pleasing to the eye can be created, a more "friendly" visual representation for the processor and/or the user, one in which gaps are fewer and easier to identify. This is particularly beneficial, for example, in situations where manual follicular unit selection is desired, situations in which for example, the user can manually select follicular units to be harvested that were missed by an automatic selection algorithm or close to the skin tensioner but still harvestable in the eyes of the user.

One way in which the gap 835 illustrated in FIG. 8(*a*) can be avoided, is by using an alternative or additional methodology which serves to fill the gaps between the exclusion zones 820, 825 and 830. In one embodiment, more than one existing follicular unit harvest site is used to create a visual representation of the exclusion zone for that particular harvested follicular unit. For example, in one such method for creating a visual representation of the exclusion zone, the visual representation is generated by using not only the newly harvested follicular unit, but by using information from its neighboring or satellite sites, the sites of previously harvested follicular units that are in close proximity to the newly harvested follicular unit.

FIG. 8(*b*) shows the two existing harvested follicular unit sites 805 and 810, and a site 815 which represents a site of a newly harvested follicular unit. For ease of explanation, the exclusion zones 820, 825 and 830 have been omitted. When processing the exclusion zone for the newly harvested follicular unit site 815, the processor is configured to determine whether or not the already existing follicular unit harvesting site 805 is within, for example, a predetermined distance from it. This predetermined distance may be based, for example, on a multiple of the minimum harvest distance described above, the multiple being greater than one, and ranging, for example, from 1.5 to 2.5. For example the predetermined distance may be less than or equal to at least twice the minimum harvest distance from the newly harvested follicular unit site 815, that is a distance of, for example, 3.8 mm. If it is found that the already existing follicular unit harvesting site 805, for example, is less than or equal to at least twice the minimum harvest distance away from the newly harvested follicular unit site 815, the already existing follicular unit harvesting site 805 may be considered to be a satellite site with respect to the newly harvested follicular unit site 815. If, however, it is found that the already existing follicular unit harvesting site 805 is more than at least twice the minimum harvest distance away from the newly harvested follicular unit site 815, the already existing follicular unit harvesting site 805 may be considered not to be a satellite site with respect to the newly harvested follicular unit site 815. In a similar manner, when processing the exclusion zone for the newly harvested follicular unit site 815, the processor is configured to determine whether or not the already existing follicular unit harvesting site 810 is less than or equal to at least twice the minimum harvest distance from the newly harvested follicular unit site 815, that is a distance of, for example, 3.8 mm.

Figure 8A:
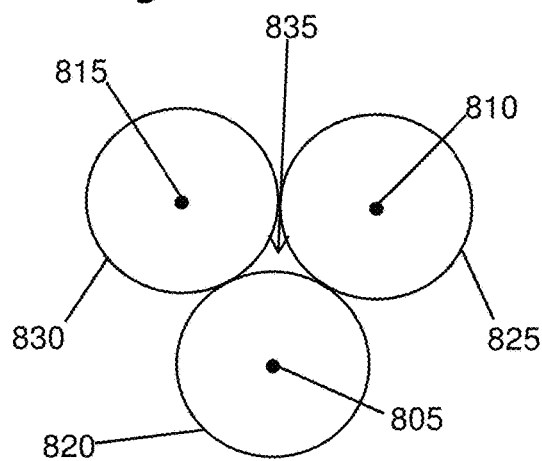
FIGS. 8(a)-(f) are schematic representations illustrating an example of the use of satellite sites in the provision of exclusion zones.
Figure 8B:
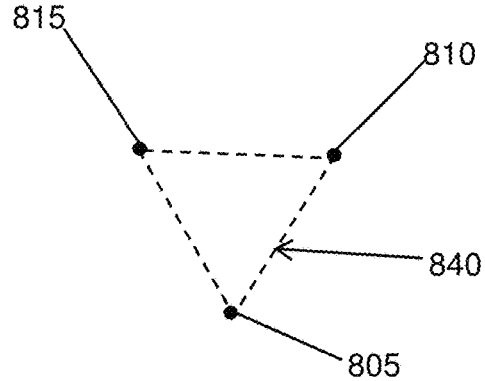
Figure 8C:
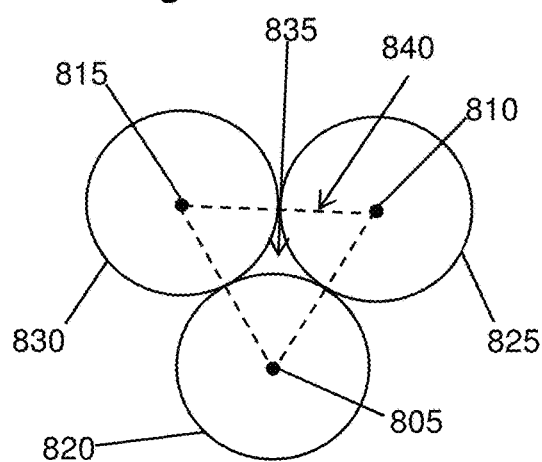
Figure 8D:
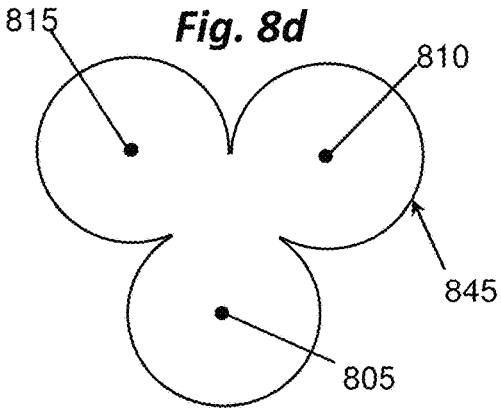

For ease of understanding, let us assume that both existing harvested follicular unit sites 805 and 810 are less than or equal to at least two times the minimum harvesting distance from the newly harvested follicular unit site 815. In this instance the processor creates a closed loop profile, or a supplemental exclusion zone, based on the locations of the newly harvested follicular unit site 815, and the existing harvested follicular unit sites 805 and 810, forming a triangular shape 840 as illustrated in FIG. 8(*b*). The processor combines or superimposes this closed loop triangular profile 840 (the supplemental exclusion zone) onto the three circular exclusion zones 820, 825 and 830, as illustrated in FIG. 8(c) to form a visual presentation of the modified exclusion zone 845, as illustrated in FIG. 8(d) that no longer incorporates the relatively small gap 835.

Figure 8E:
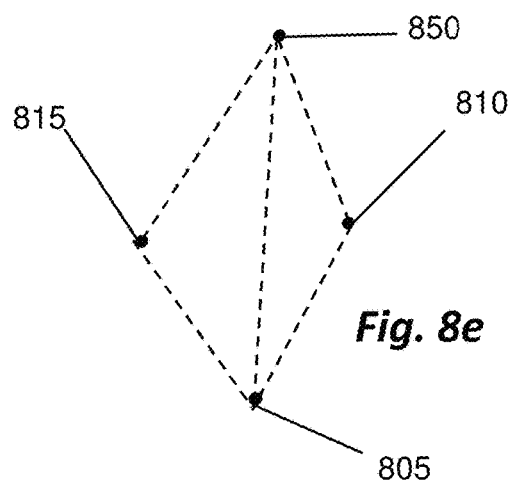

FIG. 8(e) illustrates an example in which a newly harvested follicular unit site 850 is introduced, sites 805, 810 and 815 all being already existing harvested follicular unit sites. If one assumes that the existing harvested follicular unit sites 805, 810 and 815 are less than or equal to a certain minimum harvesting distance, for example, at least two times the minimum harvesting distance, from newly harvested follicular unit site 850, they will all be considered satellite sites to newly harvested follicular unit site 850. The processor in this instance is configured to create a closed loop profile (supplemental exclusion zone), based on the locations of the newly harvested follicular unit site 850, and the existing harvested follicular unit sites 805, 810 and 815, forming a polygon with indices 805, 810, 815 and 850. However if, for example, it is determined that only existing harvested follicular unit sites 810 and 815 are less than or equal to at least two times the minimum harvesting distance from newly harvested follicular unit site 850, and existing follicular unit harvesting site 805 is more than at least two times the minimum harvesting distance from the newly harvested follicular unit site 850, only existing harvested follicular unit sites 810 and 815 will be considered satellite sites for site 850, and the close loop profile will be a triangle (not shown) with the indices of 810, 815 and 850.

Figure 8F:
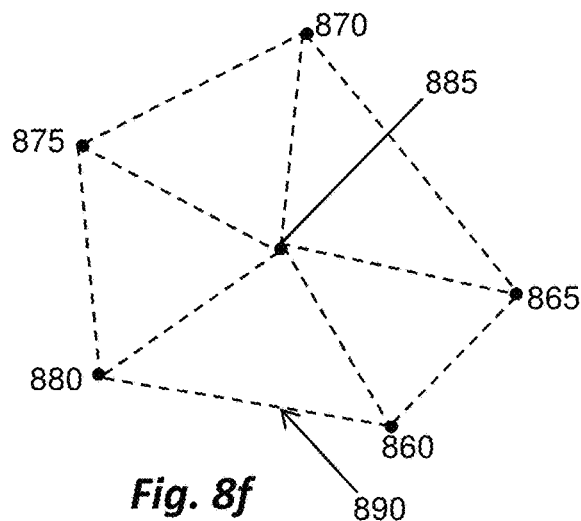

Finally, FIG. 8(f) illustrates an example in which the centrally located newly harvested follicular unit site 885 has five satellite sites 860, 865, 870, 875 and 880 around it. Rather than providing a visual representation of an exclusion zone that only comprises a simple circles surrounding the newly harvested follicular unit site 885, the processor, having determined that each of the already existing harvested follicular unit sites 860, 865, 870, 875 and 880 surrounding the centrally located newly harvested follicular unit site 885 are less than or equal to, in the provided example, twice the minimum harvesting distance from it, forms a polygon 890 (supplemental exclusion zone) linking all the satellites to surround the centrally located newly harvested follicular unit site 885. In this instance, by combining this polygon shape 890 with the six circular exclusion zones corresponding to the already existing harvested follicular unit sites 860, 865, 870, 875 and 880, no gaps are visualized within the visual representation of the modified exclusion zone. This potentially enables a reduction in computer processing time, and it also provides benefit to the user by ultimately enabling the user to more easily identify on a display and focus on the larger gaps that may exist.

Figure 9A:
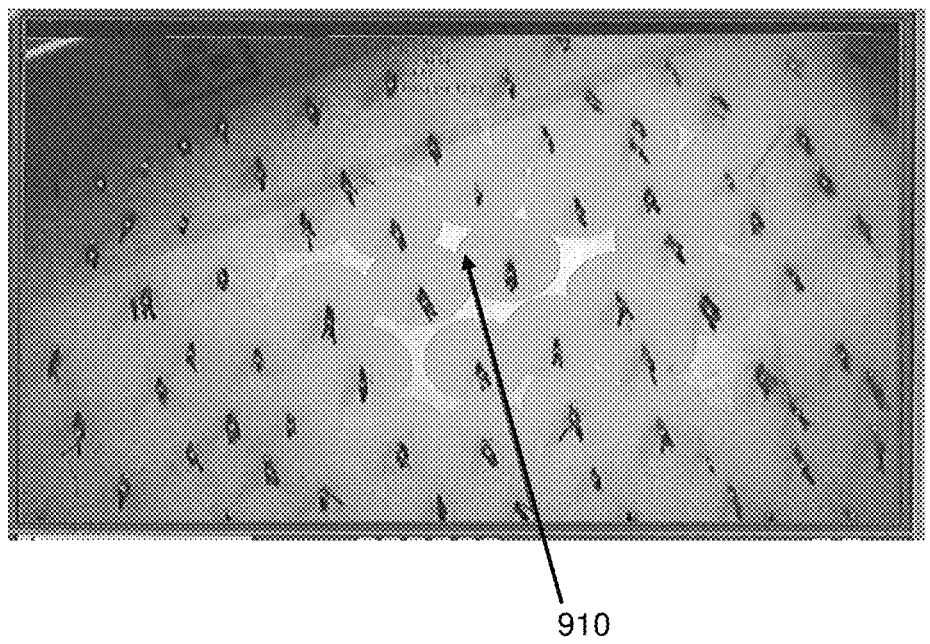
FIGS. 9(a) and (b) illustrate the difference between using and not using the satellite exclusion zone methodology.
Figure 9B:
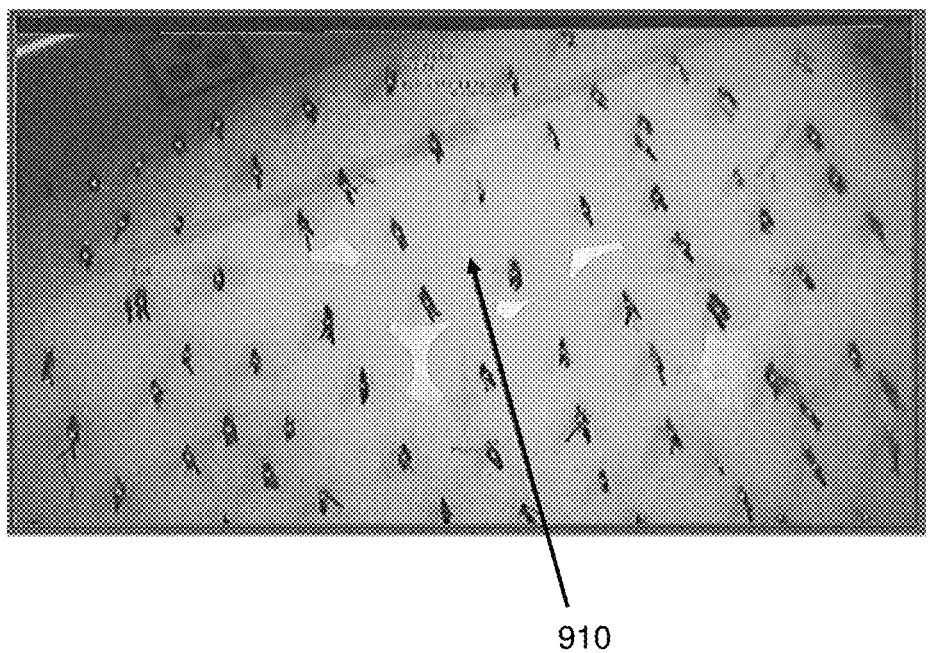

FIG. 9(a) illustrates a visual representation which only utilizes a methodology in which the exclusion zones are centered about the harvested follicular units. In FIG. 9(a) attention is drawn to one particular gap 910. On the other hand, FIG. 9(b) illustrates the visual representation which utilizes a combined methodology in which the exclusion zones are centered about the harvested follicular units and then combined with the overlay of the supplemental exclusion zone provides by the appropriate satellite sites. As seen in FIG. 9(b), the location where there used to be a gap 910 is no longer there. A visually more "friendly" image has been rendered. In summary, according to some embodiments a method is provided for generating a visual representation of a region where a procedure was performed. The method comprising generating a visual representation of one or more procedure sites (e.g. harvest sites) where a procedure was performed. If more than one procedure site exists, the visual representation of the exclusion zones for each of the procedure sites are overlapped. The method further comprises generating one or more supplemental exclusion zones for any or all procedure sites; and overlapping the exclusion zone and the supplemental exclusion zones to generate the representation of the performed procedure region. The step of generating one or more supplemental exclusion zones may be accomplished by comparing a distance between a particular procedure site and one or more previous procedure sites that surround that particular procedure site, and for those surrounding sites where the distance is within a predetermined or selected limit, such surrounding sites are identified as the satellite sites for the particular site. In some embodiments, the above-mentioned comparison may be run against every existing procedure site to identify a corresponding collection of the satellite sites for each existing procedure site. In some embodiments, with reference to hair transplantation, each new harvested hair graft may be compared to any or all other previous harvested hair grafts and be added, as appropriate, based on the results of the comparison, to a collection of the satellite sites for each relevant previous harvest site. Alternatively or in addition, any or all previous harvest sites may be compared to a newly harvested site and, based on the results of such comparison, be identified as the satellite sites for the newly harvested site. In some embodiments, the satellite sites may be sorted based on certain criteria, such as the tangle angle in the coordinate system, for example, with the smaller angle going first, forming a counter-clockwise sequence, or with a greater angle going first, forming a clockwise sequence. This sorting may be used to generate a continuous convex profile. Without sorting, the random sequencing of the satellite sites may miss some parts of the geometry profile. In some embodiments, the method may further comprise updating and displaying the previous procedure region.

Figure 10:
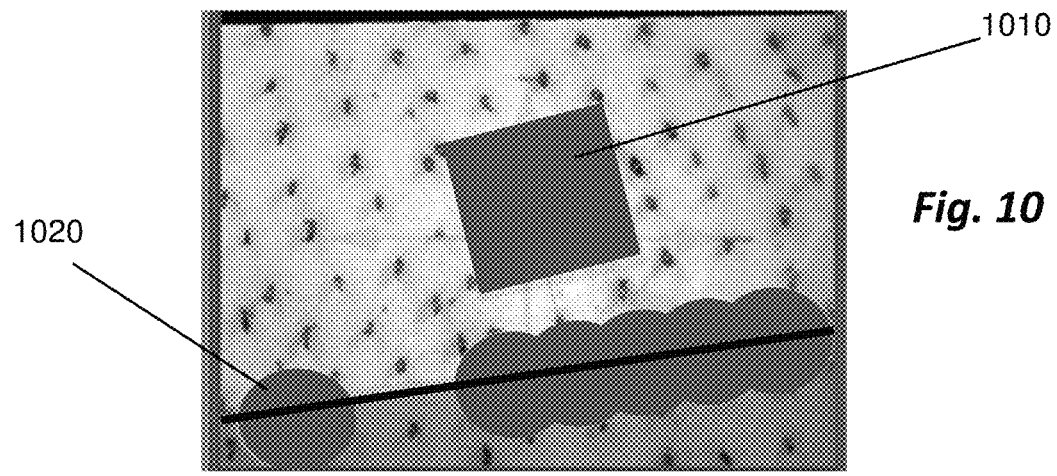
FIG. 10 is an example of a schematic representation of a reserved harvesting region.

It may be desirable in various procedures to identify "reserved regions" where procedure should not be performed. These reserved regions will be described in reference to hair harvesting and implantation and therefore will be referred to the "reserved harvest regions", however, it should be understood that this description applies to various "reserved regions" for various medical procedures within the scope of the inventions described herein. Reserved harvest regions define areas from which hairs are not to be selected for harvesting. These reserved harvest regions may define areas where skin conditions exist that make the area unsuitable or undesirable for harvesting from or implanting into, areas which contain previously implanted follicular units, areas containing a particular classification of follicular unit (such as F1 for example) that are not desired for the current harvest, areas where moles or scars exist, or define areas exhibiting any number of other conditions. These reserved harvest regions can be illustrated, as shown, for example, in FIG. 10, as a box 1010, or as a circular representation (note that if a circular representation is used, the circles representing the reserved harvest regions may be formed in a different color than the circles used to identify the exclusion regions 1020), or as any arbitrary shape, and may be created in numerous ways. For example, the user may manually define a reserved harvesting site by manually clicking a mouse at a point within the revised boundary 410, to create a reserved harvest region box of pre-defined size. Alternatively, a reserved harvest region box may be created whose sides may be adjusted by the user, or several points may be identified by the user, and the processor may create a closed-loop arbitrary shape that encompasses all the identified points. In an alternative, the reserved harvest regions may be automatically created by the processor once it has processed the information contained in the acquired images, and the user may be allowed to accept or reject these automatically created reserved harvest regions. It will be apparent that there are many other ways in which such reserved harvest regions may be created for or by the user.

Returning to the discussion of the fiducials, sometimes not all the fiducials are visible in the frame of view of the camera. For example, there may be situations in which all of the fiducials are not visible, and only a subset of them is. In this embodiment of the invention, the system may use the limited information initially available and ultimately create a register of the location of all the fiducials with respect to each other.

Figure 5A:
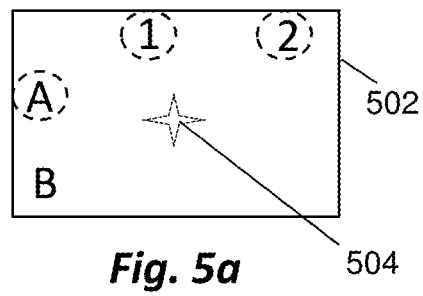
FIGS. 5(a)-(g) show an example of identifying and recording fiducials as could be implemented in an example of the embodiment of the invention.

According to another aspect of the present application, examples of locating and registering a plurality of fiducials are described in reference to FIGS. 5(a)-5(g). With reference to the example of the robotic system of FIG. 2, since the field of view of the cameras (for example, 2 cameras used for stereovision) may be smaller than the area spanned by the fiducials, it may be necessary to move the robot around the boundary (e.g. perimeter of the tensioner or a region defined by a pattern of existing hairs acting as fiducials) to capture the locations of the fiducials. This motion may be performed, for example, manually by an operator's hand dragging the imaging mechanism attached to the robotic arm using "force-control", or by manipulating the robotic pendant. However, in a preferred embodiment, a robotic arm with the attached image acquisition device may be moved automatically around the periphery of the skin tensioner (or around the boundary with a plurality of fiducials that defines the harvesting or implantation region). In the automated approach, the robot may be first moved manually to the initial position which brings enough fiducials into view to establish the fiducial frame of reference. Typically, it requires at least three (3) fiducials. FIG. 5(a) illustrates an initial frame of view 502 taken from the frame of view of the camera(s) which is mounted on a robotic arm of a follicular unit harvesting or implanting system, the frame of view having a center point of reference 504. In this embodiment, four fiducials A, B, 1 and 2 are visible in the initial frame of view 502. In order to utilize the teachings of this invention, the system has to acquire the location and/or orientation of each fiducial with reference to at least one other fiducial. As mentioned above, in order to obtain information pertaining to both location and orientation, at least three fiducials are required to be visible in the initial frame of view 502. For example, some examples of obtaining, tracking and recording information about fiducials that could be used in the present invention is described in the commonly owned co-pending patent application published as US 2010-0080415A1 on Apr. 1, 2010, which is incorporated herein by reference.

Figure 5B:
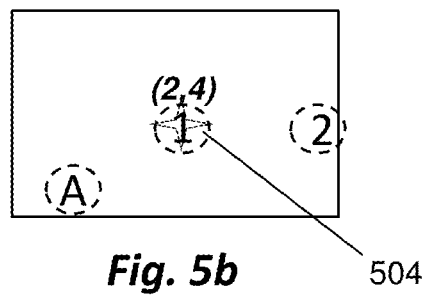

To enable the system to acquire the location and optionally the orientation of the other fiducials, the system initially moves the field of view of the camera over the body surface such that one of the fiducials that was in the initial frame of view 502, is located at the center of the frame of view, that is, that the centroid of fiducial 1 is substantially aligned with the point of reference 504, as shown in FIG. 5(b). This first fiducial 1 is allocated location and optionally orientation coordinates, for example it may be given the reference coordinates of (2, 4). The image processor subsequently identifies the next closest fiducial that has not already been centered. In the event that there are two or more closest fiducials, the system is configured to select the closest fiducial according to a predetermined selection mechanism. The selection mechanism may be relatively simple, such as always selecting the one towards a particular direction, and only doing so if the reference coordinates of the fiducial in that direction have not already been acquired. In this instance, the selection mechanism hierarchy may comprise, for example, the order of to the right, downwards in direction, toward the left and finally upwards in direction.

Figure 5C:
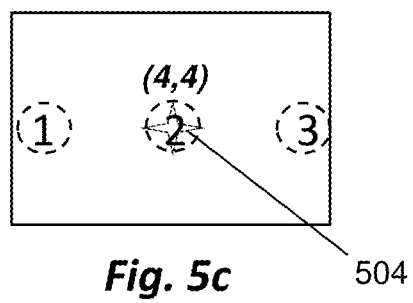
Figure 5D:
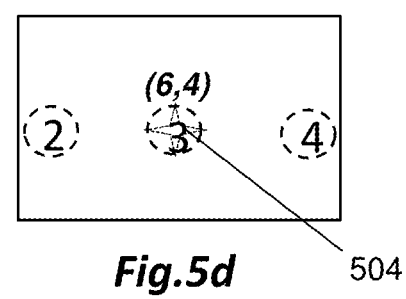
Figure 5E:
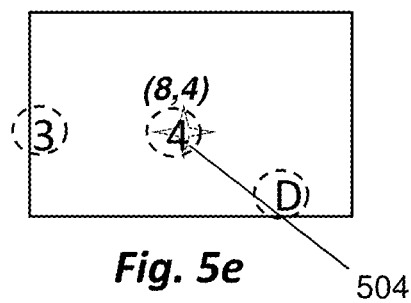
Figure 5F:
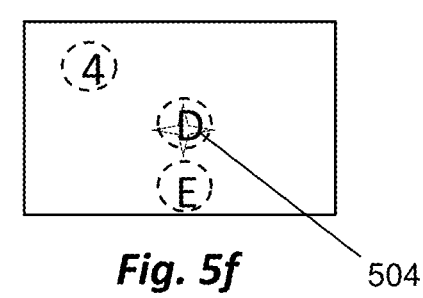
Figure 5G:
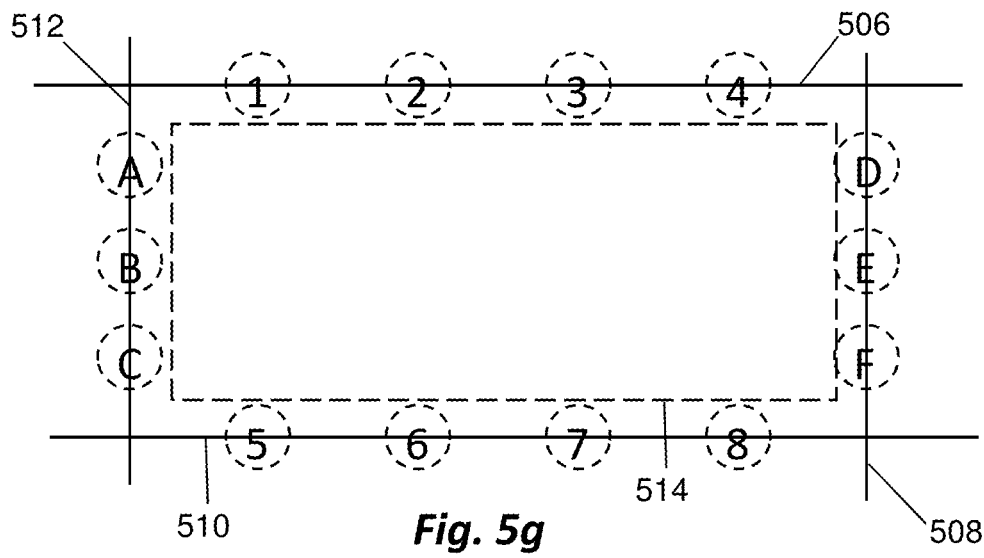

FIG. 5(c) illustrates the camera having been moved over the body surface such that the centroid of the closest fiducial 2, to the right hand side of the fiducial 1 is located at the reference location 504 of the field of view 502. In order to get to this particular location, the movement undertaken by the camera itself is registered. For example, if the camera movement from a position where the centroid of fiducial 1 was at the point of reference 504 to a position where the centroid of fiducial 2 was at the point of reference 504, is defined by (2,0), then the coordinate for the location of the centroid of fiducial 2 would be (4, 4). Similarly, in FIG. 5(d) the camera movement from a position where the centroid of fiducial 2 was at the point of reference 504 to a position where the centroid of fiducial 3 was at the point of reference 504, as (2,0), then the coordinate for the location of the centroid of fiducial 3 would be (6, 4). It can be seen that in FIG. 5(e), once the centroid of fiducial 4 is placed at the point of reference 504, and allocated the coordinates (8,4) there is no fiducial to the right, and in FIG. 5(f), the camera is moved (2,−1) such that the centroid of fiducial D is at the point of reference 504. In this manner, the location of the centroids of all fourteen distinguishable fiducials (shown in FIG. 5(g)) are known with respect to each other. In possession of this information, in some embodiments virtual lines 506, 508, 510 and 512 may be drawn to define an initial boundary, and after taking into account the location of the centroids of the fiducials, for example, from the inner edges of the tensioning device, the relative height of the tensioning device above the body surface (assuming an embodiment where there is one) and/or the tool diameter, a revised boundary 514 can be determined, inside of which the coordinates of follicular unit can be identified for harvesting, or the coordinates of follicular unit implantation sites can be identified for implantation.

According to one embodiment of the method of the invention, an initial image and one or more successive images are taken of a skin surface containing a plurality of fiducial marks. In each successive image, the offset of the fiducials from their positions in the initial image is recorded by computing, for example, a best-fit transformation T that minimizes the error between the original positions and the transformed value of the subsequent positions. If new fiducials are seen in subsequent images, their positions are transformed by the inverse of T so that they too can be recorded in the frame of reference of the initial image. Once their location is transformed and recorded, these new fiducials can then be used in conjunction with the original fiducials to locate an update to the best-fit transformation T. This fiducial offset information is utilized in processing the location and/or orientation, for example, of a harvesting site, applying the offset to the intended harvesting location prior to carrying out the harvesting itself. Similarly, the fiducial offset information could be used in processing locations and/or orientations of the intended implantation sites and such offset could be applied to the intended implantation location prior to actual implanting.

Having created a set of coordinates for carrying out the harvesting or implanting procedure, as long as a couple of fiducials can be seen in the frame of view, the procedure can be carried out, using the visible fiducials as reference points. In the case where the field of view is isolated from the fiducials, harvesting locations from where follicular units have already been harvested or implantation sites into which follicular units have already been implanted can be used to supply additional reference points, to which future harvesting or implantation locations can be referenced.

In one example of the embodiment of the invention, a method is provided that allows defining a region over which a tool is to be operated, for example, to harvest or implant hair grafts. In one preferred embodiment, such method may be substantially automated (which means that at least most of the steps could be performed automatically by the robotic system itself). It does not exclude that a user may intervene and participate, for example, by giving an alternative command through a user interface, or override the automated command. Generally, if a robotic system, similar to a system shown by example in FIG. 2 is used, an operator may initiate an automatic procedure as follows. One of the fiducials that was previously identified may be arbitrarily chosen. The robotic arm with a camera operatively connected to it may move automatically to center the fiducial in the field of view of the camera. As long as spacing between the fiducials is less than half of the field of view, this will assure that at least two fiducials will be visible. The processor may then direct the robotic arm with the camera to choose the next closest fiducial that has not already been centered. In the same fashion, the robotic arm will continue to move automatically to the next fiducial to center the next fiducial until all fiducials have been identified. If the fiducials are located on the skin tensioner, then the robotic arm will be directed to move around the skin tensioner. Once all relevant fiducials are registered in the fiducial frame of reference, if desired, the boundary of the region defined by the fiducials may be automatically computed by the processor, and furthermore such boundary may be adjusted so that a tool (e.g., harvesting needle) may safely access follicular units inside the boundary. The start and the initial harvest position and direction may be computed automatically by the automated system. To minimize any potential interference of saline and/or blood in the field of view, the processor may be programmed to start harvesting or implanting from the edge of the boundary with the lowest height and close to the corner. The robotic arm is directed to automatically move with the attached tool to harvest or implant hair grafts within the boundary.

Figure 6A:
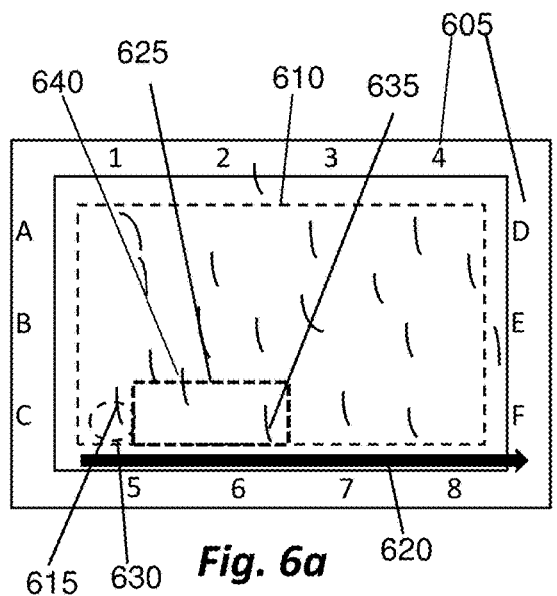
FIGS. 6(a)-(f) show another example of implementation of the methodology according to an embodiment of the invention.

FIGS. 6(a)-6(f) demonstrate an embodiment according to another implementation of the invention which uses a defined virtual selection region. The tool may be moved automatically within such selection region as explained below based on desired criteria. Let us assume, for the purposes of this particular discussion, that the revised boundary 610 has dimensions, for example, in the region of 4 cm horizontally and 3 cm vertically. Having established coordinates of the fiducials (such as fiducials 605 illustrated in FIG. 6a), as described in earlier examples, the tool is operated (for example, automatically or semi-automatically) to initiate the harvesting procedure from the bottom left hand corner of the revised bound area. For example, the tool may be operated to move to the location that is approximately at the intersection of row C-F and column 1-5, and aligned with the follicular unit 615. The processor at this time may also dictate that the tool be moved in the general direction of arrow 620, away from the location of fiducial C and towards fiducial F, in a horizontal direction substantially parallel to a horizontal side of the revised boundary 610. Based on the exact coordinates of the tool's location with respect to the image frame of reference, the processor may compute virtual boundaries of a smaller virtual selection region 625 located just in front of the tool in the direction of travel 620. In this particular illustrated example, the virtual selection region 625 may comprise a quadrilateral, such as a rectangle having, for example, dimensions of 6-8 mm by 3.5-4.5 mm. Other dimensions of the selection region 625 are also contemplated within the scope of this application. Use of a smaller virtual selection region 625 reduces the computation required to find a subsequent follicular unit to harvest by restricting the area of consideration to an area just in front of the previous harvested follicular unit 615 and along the direction of travel 620. The tool is operated to harvest the follicular unit 615 and the location of the harvested follicular unit 615 is visually identified, for example, by a circle 630, as seen in FIG. 6(a). After harvesting the follicular unit 615 the harvesting tool is moved in the general direction of the arrow 620, and operated to harvest one or more follicular units located within the virtual selection region 625. As seen, there are several follicular units located within the region 625. However, the next selected follicular unit for harvesting may be not the follicular unit located within the shortest distance from the harvested follicular unit 615 inside the region 625 (such as follicular unit 640), but may instead be based on predetermined selection criteria, such as in this example where the tool is moved to the location of the follicular unit 635 that is the closest to the horizontal boundary 610.

Figures 7A, 7B:
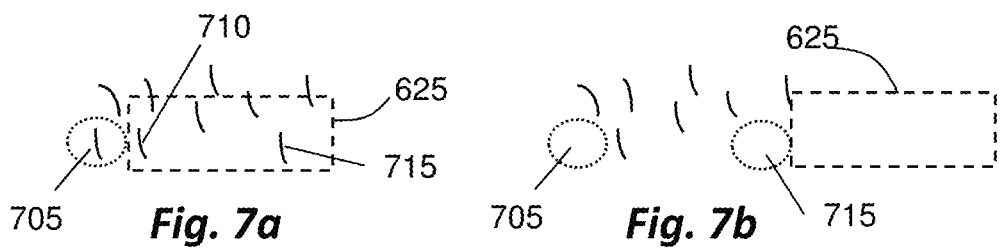
FIGS. 7(a)-(f) illustrate examples of various selection criteria according to various embodiments of the invention.
Figures 7C, 7D:
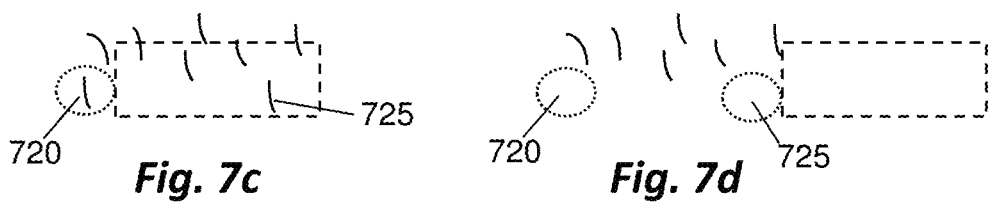
Figures 7E, 7F:
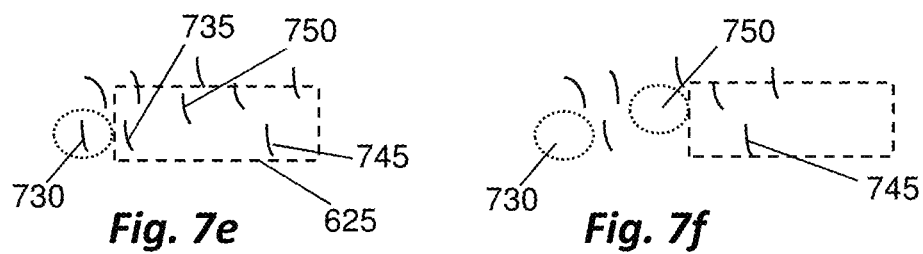

Examples of a few criteria that could be used in directing movement of the tool within the selection region (such as region 625 of FIG. 6(a)) are described with reference to FIGS. 7(a)-7(e) below, but it will be appreciated that many other criteria may be chosen or predetermined, and such criteria may vary during the hair transplantation process. In FIGS. 7(a) and 7(b), three follicular unit s have been identified within the selection region 625, follicular units 705, 710 and 715. One particular selection criteria may be, for example, such that if follicular unit 705 is harvested, the system will be operated to harvest follicular unit 715, and leave 710 un-harvested, effectively harvesting every other follicular unit. Another or an additional predetermined selection criteria, as illustrated in FIGS. 7(c) and 7(d), if follicular unit 720 is harvested, may be to harvest every other follicular unit within the selection region except when the distance to the next available follicular unit exceeds certain predetermined distance. In the example of FIGS. 7(c) and 7(d), even though follicular unit 725 is the next available follicular unit, it is harvested because it is located at a distance, for example greater than 1.9 mm away, from the already harvested follicular unit 720. As seen in FIG. 7(b), once the follicular unit 715 has been harvested, a new virtual selection region 625 is created next to the harvested follicular unit in the same direction of travel. Turning now to FIGS. 7(e) and 7(f), in this illustration, once follicular unit 730 has been harvested, follicular unit 735 is left un-harvested, and although follicular unit 745 is the next available follicular unit in the horizontal direction, it too is left un-harvested. In this example, the predetermined selection criteria is set such that the next follicular unit available can be selected whether it be the next available closest in the horizontal or the vertical direction, provided that it is contained within the virtual selection region 625. Consequently, follicular unit 750 is harvested, as indicated in FIG. 7(f).

Figure 6B:
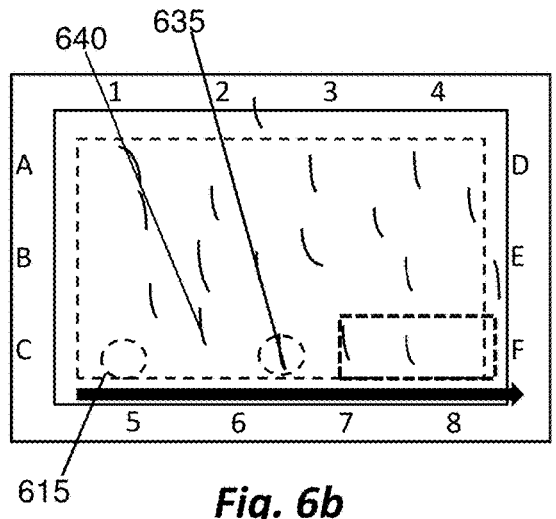
Figure 6C:
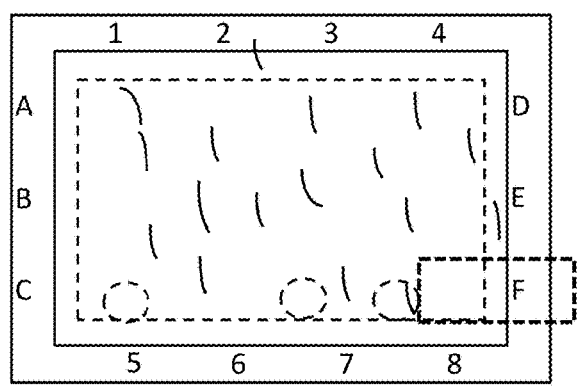
Figure 6D:
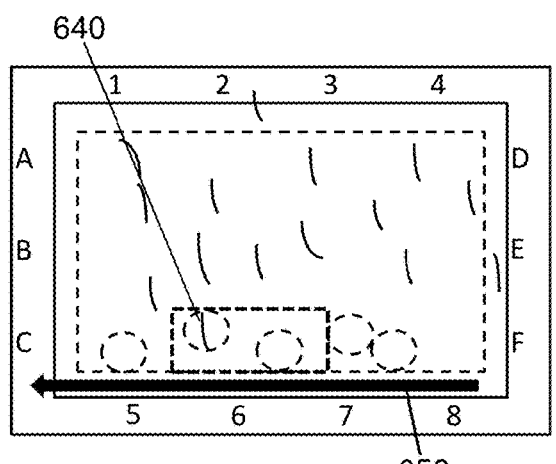
Figure 6E:
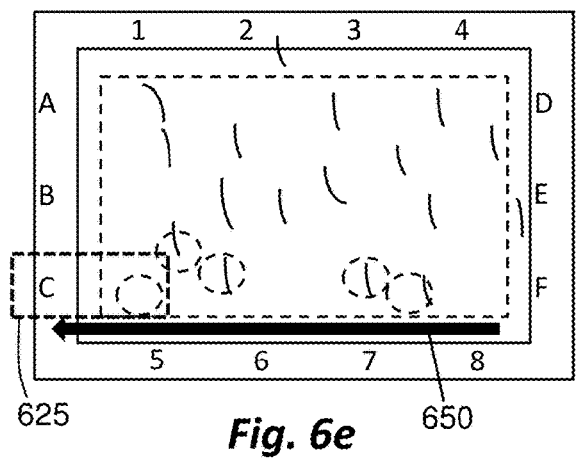
Figure 6F:
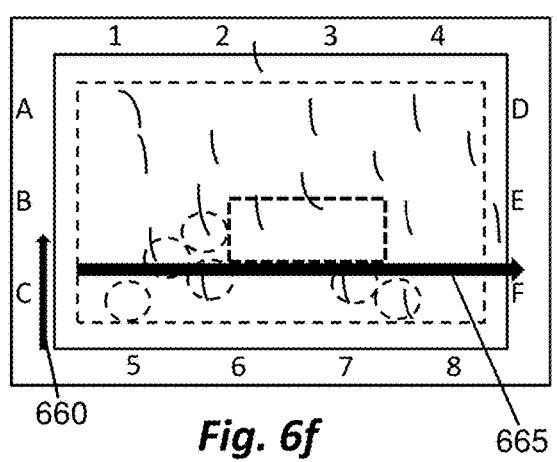

Returning now to the example we were discussing in FIG. 6(b), it can be seen that the follicular unit 640 was too far in the vertical direction from the horizontal boundary 610, and it was therefore not a desirable follicular unit to harvest at this time. The system, as shown in FIG. 6(b) illustrates follicular unit 640 still on the patient's body surface, and follicular unit 635 being harvested. On reaching the fiducial F, as illustrated in FIG. 6(c), the image processor ascertains that the revised vertical boundary has been reached, and provides the control signals necessary for the robotic arm to move in the direction of arrow 650, as shown in FIG. 6(d). If desired, the movement of the tool in the direction of arrow 650 will allow the harvesting tool to harvest the follicular unit 640 that was previously left un-harvested. In FIG. 6(e), it can be seen that the virtual selection region 625 is moved in the direction 650 along the row F-C until all desired follicular units in that row are harvested. When no desired follicular units remain to be harvested within the desired "harvest quadrilateral" along the current row, the tool is operated to move in an upwardly direction 660 and towards the right, in the direction of arrow 665, to harvest follicular units in the row B-E in a similar manner, as illustrated in FIG. 6(f). Since hair and fiducials are in the same frame, it can be computed to determine whether the current harvest row needs to be incremented: move to the new row when there are no remaining hairs in the current row within the "harvest quadrilateral" formed by lines a specified distance away from the rows of fiducials. In the example of the robotic application, as the robot moves an automated harvesting (or implanting) tool along a current row and approaches a corner along the edge or boundary, the robotic system reverses direction and starts searching along a row spaced a configurable distance toward the opposite edge.

Although the embodiment illustrated and described above with respect to FIGS. 6(a)-6(f) describes that follicular units are harvested within the virtual selection region until no desired follicular units remain to be harvested within the desired "harvest quadrilateral" whereupon the virtual selection region is incremented to the next row, it is understood that this is an example. Other procedures are possible and contemplated without departing from the scope of the present disclosure.

By way of an example, in some implementations, follicular units may be collected by proceeding along a row and then automatically incrementing to the next row. However, in some cases, a harvest target of harvesting a particular percentage of follicular units within an area of skin may be established. For example, a harvest target of harvesting 50% of the follicular units within an area of skin may be established. In order for this harvest target to be achieved, a follicular unit row target of approximately 10 follicular units may need to be harvested within each row into which the area is divided. However, if the row is automatically incremented when the end of a row is reached, the follicular unit row target of 10 follicular units (and thereby the harvest target of 50%) may not be achieved.

In another example, the area may be divided into rows and follicular units within a row (such as the row located at the bottom of the area) may be harvested (such as within a virtual selection region moved along the row and/or moved back and forth along the row) until a particular target of the numbers of the follicular units for the row is reached. In some cases, the determination as to whether or not the follicular unit row target (such as 10 follicular units) for the row is reached may be made at the end of the row. In other cases, the determination may be made at other times, such as subsequent to each time a follicular unit is harvested. Regardless, if the follicular unit row target has not been reached, harvesting continues within the row. However, if the follicular unit row target has been reached, harvesting may continue at the next row.

Although this example describes incrementing the row from which follicular units are to be harvested only if the follicular unit row target for the row has been precisely met, it is understood that this is for the purposes of example. In other implementations other procedures are possible and contemplated without departing from the scope of the present disclosure. For instance, in some cases, a certain number that is less than the follicular unit row target may be harvested from one or more rows of the area while still achieving the overall desired target number for the area. In such cases, the row may be incremented if the number of follicular units that have been harvested is within a range of the follicular unit row target for the row, or a desired percentage of an area of skin.

For example, a harvest target of 75% may be set for an area of skin. To achieve the harvest target, an average of 15 follicular units may need to be harvested from each row into which the area has been divided, some rows providing more than average 15 and some less than average 15 follicular units, as long as the actual number of follicular units harvested in the relevant area averages 15 follicular units per row. In another example, during processing of a row, a comparison may be made between the number of follicular units that have been harvested and the follicular unit row target of 15. A threshold range above and below the target number may be established in certain embodiments. If the number is above a lower threshold value (such as within three follicular units of the target 15, or at least 12), the row may be incremented. However, if the number is below the lower threshold (less than 12 if the threshold is three follicular units), harvesting may continue within the current row. Similarly, the row may be incremented when the upper threshold value of the range of the desired target number is achieved.

The above description of incrementing rows is discussed within the context of harvesting follicular units. However, it is understood that this is for the purposes of example and such row incrementing is not limited to harvesting of follicular units. In various implementations, such techniques may be used in the context of transplanting follicular units, other medical procedures, and so on without departing from the scope of the present disclosure. Further, although the above description refers to 'rows,' it is understood that a row as discussed herein does not refer to a straight line. A 'row' may be any portion of a selection region of some width and follicular units may be positioned within such row in a way that is not uniform (i.e., follicular units may be positioned slightly higher than others, slightly lower than others, at various distances from each other, and so on).

The embodiments illustrated and described above with respect to FIGS. 6(a)-6(f) and FIGS. 7(a)-7(e) illustrate a number of criteria for selecting follicular unit harvesting or implantation sites. However, it is understood that these criteria are provided for the sake of example and are not intended to be limiting. Follicular unit harvesting or implantation sites may be selected according to a number of different methods without departing from the scope of the present disclosure.

FIGS. 12(a)-12(h) illustrate a number of different methods for selecting follicular unit harvesting or implantation sites in order to closely pack such follicular unit harvesting or implanting sites in accordance with various embodiments of the present disclosure. FIGS. 12(a)-12(h) are illustrated and described below as involving harvesting of follicular units. However, it is understood that this is for the purposes of example and the techniques disclosed may be utilized in the context of implanting follicular units and/or other medical procedures.

Figure 12A:
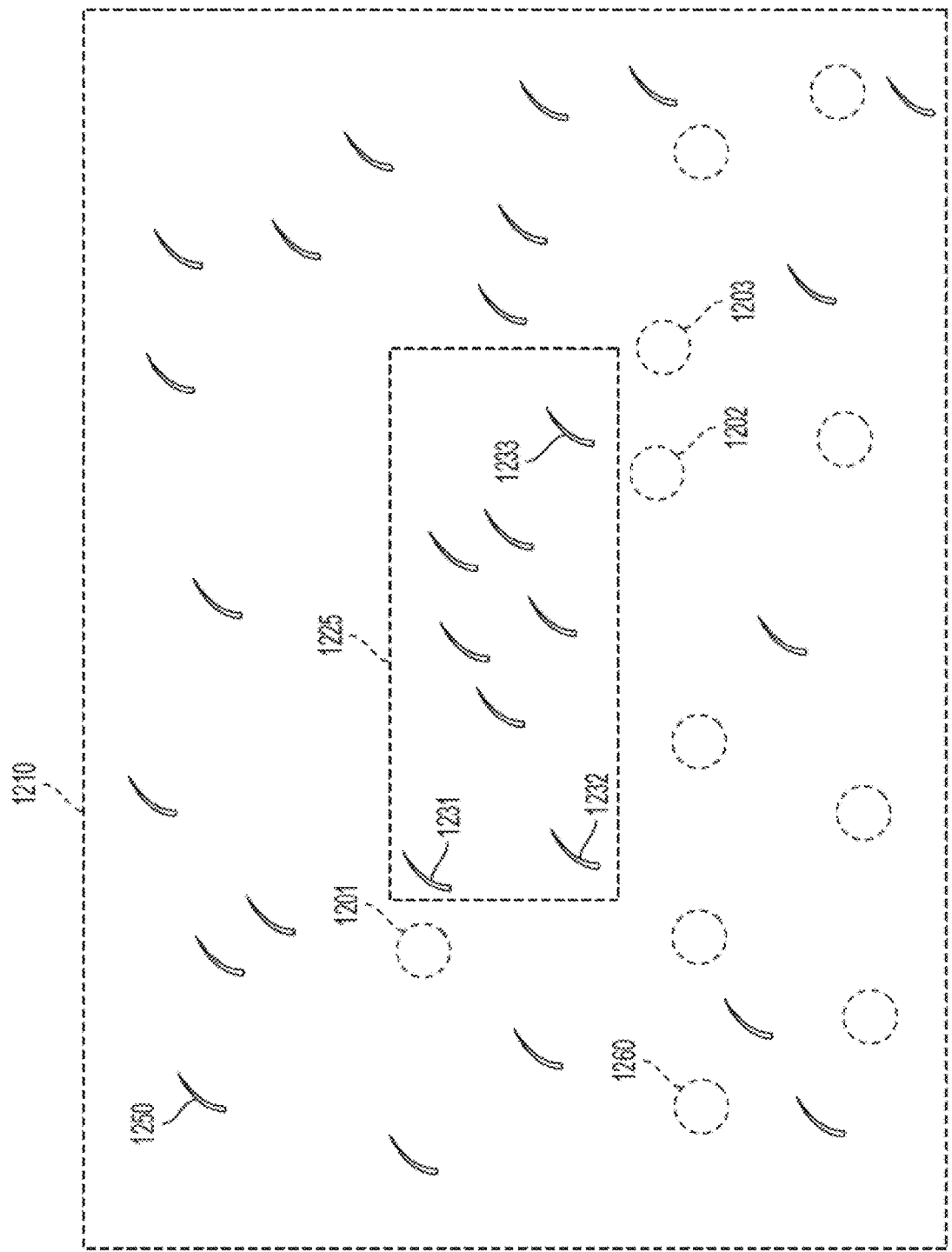
FIGS. 12(a)-12(h) illustrate a number of examples of different methods for selecting follicular unit harvesting or implantation sites that may be used with various embodiments of the present disclosure.
Figure 12B:
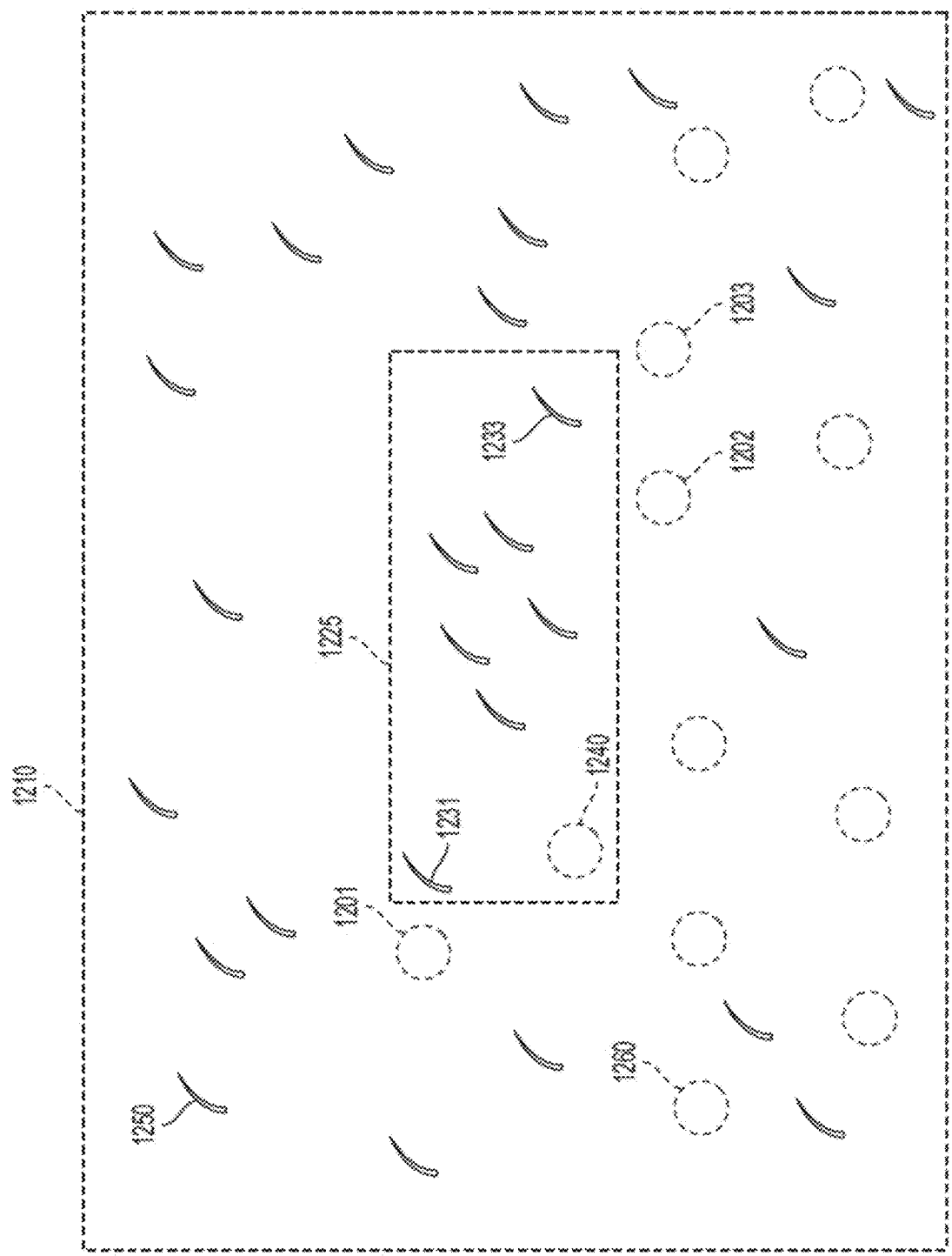

FIG. 12(a) illustrates follicular units 1250 on the skin of a patient within a boundary 1210. Circles 1260, 1201, 1202, and 1203 illustrate sites where follicular units have already been harvested. Within the boundary 1210, follicular units for harvesting may be made from within a virtual selection region 1225 which may be moved, for example, from left to right across rows beginning at the bottom left and proceeding to the top right of the boundary 1210. As illustrated, a number of follicular units (including 1231, 1232, and 1233) are within the virtual selection region 1225 and are therefore candidates for harvesting.

In some cases, follicular units may be selected using a 'lowest and closest' method. The lowest and closest method may select follicular units that are the lowest in the virtual selection region 1225 and closest to the current position of the harvesting tool in order to minimize harvesting tool movement in order to harvest follicular units. The harvesting tool may be aligned with the bottom left of the virtual selection region 1225. In FIG. 12(a), the follicular unit 1232 may be the lowest and closest follicular unit to the bottom left of the virtual selection region 1225 (i.e., the current position of the harvesting tool). As such, the follicular unit 1232 may be selected and harvested (as is illustrated by the circle 1240 in FIG. 12(b)).

However, selection of follicular units using the lowest and closest method may not result in a particularly close packing of harvest sites (i.e., some of the closely located follicular units may be ignored because they are not "the lowest" which will result in less than desired number of the selected follicular units). To improve the packing of the harvest sites, for example, to achieve the higher number of the harvested or implanted follicular units within the row, in various cases, follicular units may be selected using various enhancements, including without limitation an 'overlap priority' method, a 'position priority' method, a pattern-based method, such as 'triangular pattern priority' method, and/or a combination of these methods. It is understood that any of these methods and/or combination of these methods may also use the lowest and closest method to select between multiple candidates identified by the respective method or combination of the methods. Such methods may result in a closer packing of harvesting sites than selection utilizing the lowest and closest method.

According to an example of the 'overlap-based' or 'overlap priority' method, exclusion zones may be identified around previous harvest sites inside which follicular units will not be selected. Potential exclusion zones for follicular unit harvesting candidates may also be identified. Overlap between the existing exclusion zones for already harvested follicular units and the potential exclusion zones for the future candidates follicular units may then be analyzed to select or eliminate certain follicular unit harvesting candidates.

Figure 12C:
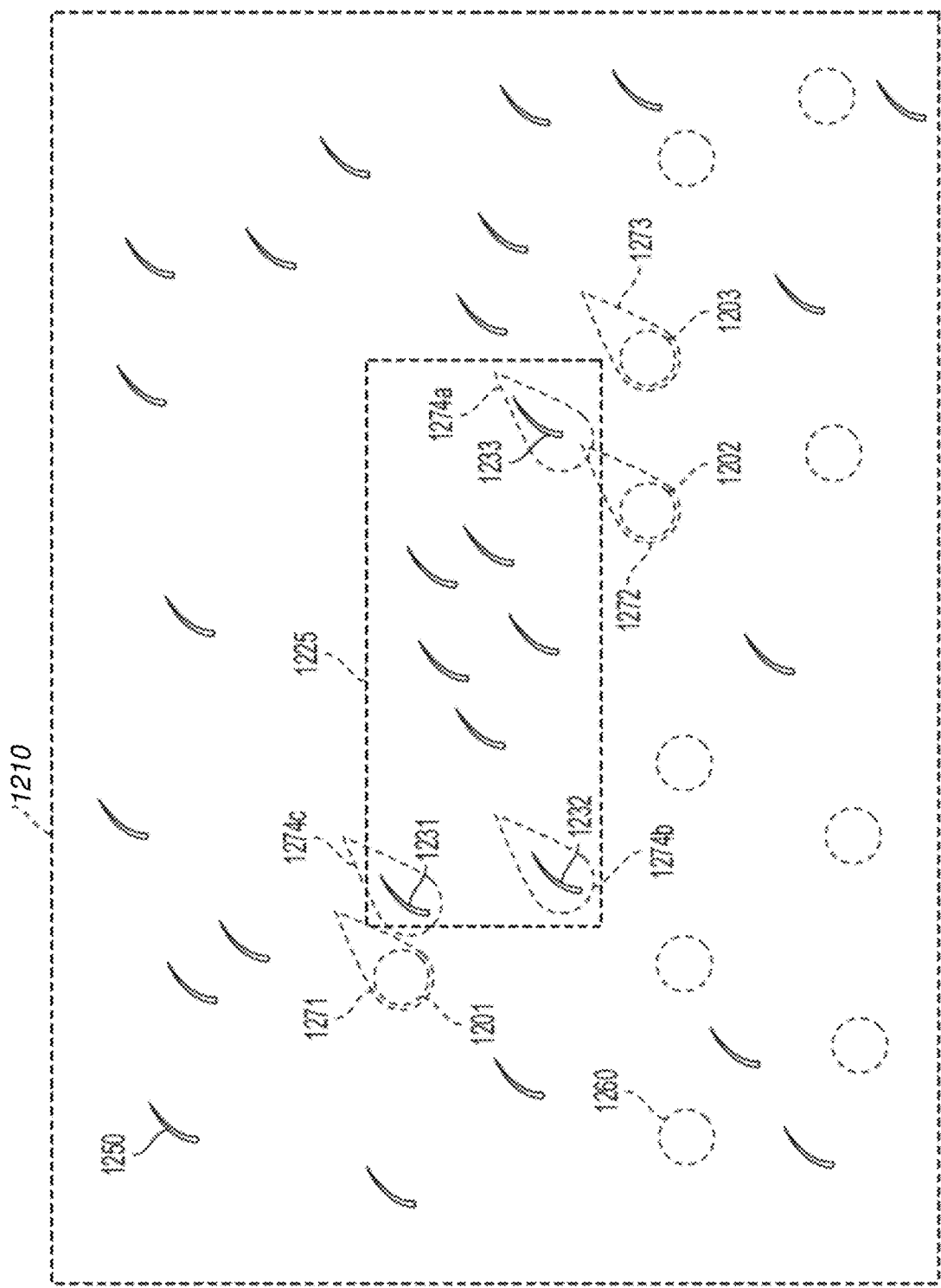
Figure 12D:
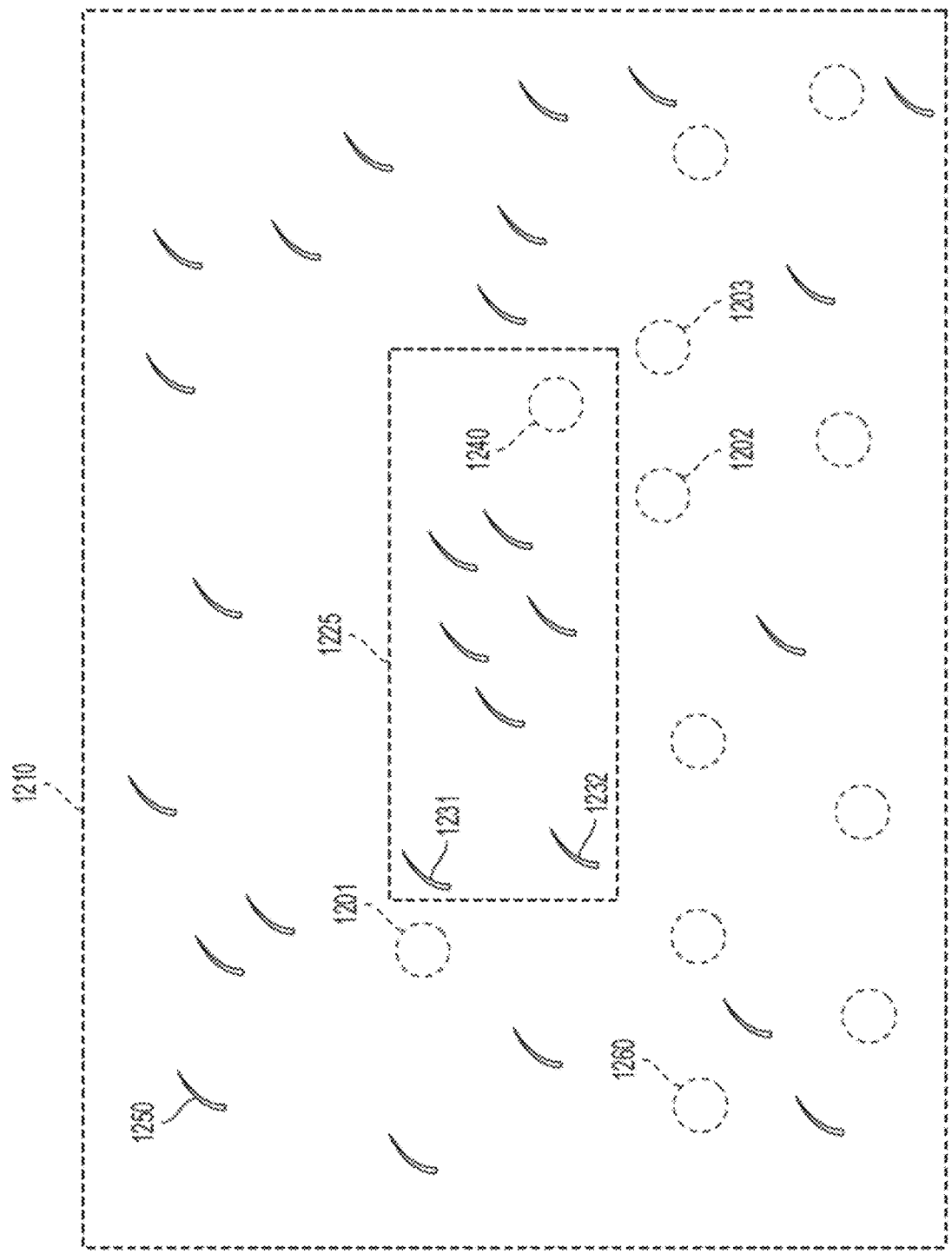

FIG. 12(c) illustrates exclusion zones 1271, 1272, and 1273 around previous harvest sites 1201, 1202, and 1203, respectively. FIG. 12(c) also illustrates potential exclusion zone 1274a around harvesting candidate 1233, potential exclusion zone 1274b around harvesting candidate 1232, and potential exclusion zone 1274c around harvesting candidate 1231. As FIG. 12(c) shows, only potential exclusion zone 1274a overlaps in any way with any of the exclusion zones 1271, 1272, or 1273, while the harvesting candidate 1233 itself is not within any of the exclusion zones 1271, 1272 or 1273. As such, the follicular unit harvesting candidate 1233 is selected for harvesting (as is shown in FIG. 12(d)). In some applications, for example, the candidate follicular unit that does not fall within the exclusion zone of a harvest site, and has the most overlap between the potential exclusion zone and the existing exclusion zone may be selected for harvesting.

The following example formula may be used in some implementations to determine whether or not the exclusion zone of a harvesting candidate has overlap with an exclusion zone from a previous harvest site:

$$\text{Objective} = \sum_{if\ distance(i) < 2*minDistance} (2 * minDistance - \text{distance}(i))^2$$

In the above example formula, minDistance may be a pre-set value (such as 1.6-2.0 mm) to define, for example as shown in FIG. 12(c), the radius of a circle, for example, from a center of the previous harvest site. If the distance(i) between a candidate harvesting site and the previous harvest site is less than 2 times minDistance, the two circles (each centered on the respective follicular unit, or location of previously harvested follicular unit, with radius of minDistance) have overlap. The formula determines how much the overlap is. If distance is small, this determined overlap will be higher. If distance is large, for example, 2 times minDistance, the value will be 0, which means no overlap. As stated above in the formula, as long as distance (i) is less than 2 times minDistance, the formula is useful to determine how much overlap exists and if there are hairs that meet this condition.

However, in some instances, no potential exclusion zones may overlap with existing exclusion zones. In such an instance, a follicular unit harvesting candidate may be selected utilizing the lowest and closest method.

Further, in various instances, a number of potential exclusion zones may overlap with one or more existing exclusion zones. In such instances, selection among follicular unit harvesting candidates corresponding to the overlapping potential exclusion zones may be performed utilizing various criteria. In some cases where a number of potential exclusion zones overlap with one or more existing exclusion zones, a follicular unit harvesting candidate may be selected utilizing the lowest and closest method.

In another case, the follicular unit harvesting candidate that corresponds to an overlapping potential exclusion zone may be selected if that follicular unit harvesting candidate is the lowest in the virtual selection region 1225 and closest to the current position of the harvesting tool out of all the follicular unit harvesting candidates corresponding to the overlapping potential exclusion zones. This extension/modification of the overlap method may be referred to as the 'overlap-based lowest and closest' or 'overlap priority lowest and closest' method.

In still another case, the follicular unit harvesting candidate that corresponds to an overlapping potential exclusion zone may be selected if the potential exclusion zone corresponding to that follicular unit harvesting candidate overlaps more existing exclusion zone(s) than any other potential exclusion zone. This extension to the overlap method may be referred to as the 'max overlap priority' method.

Figure 12E:
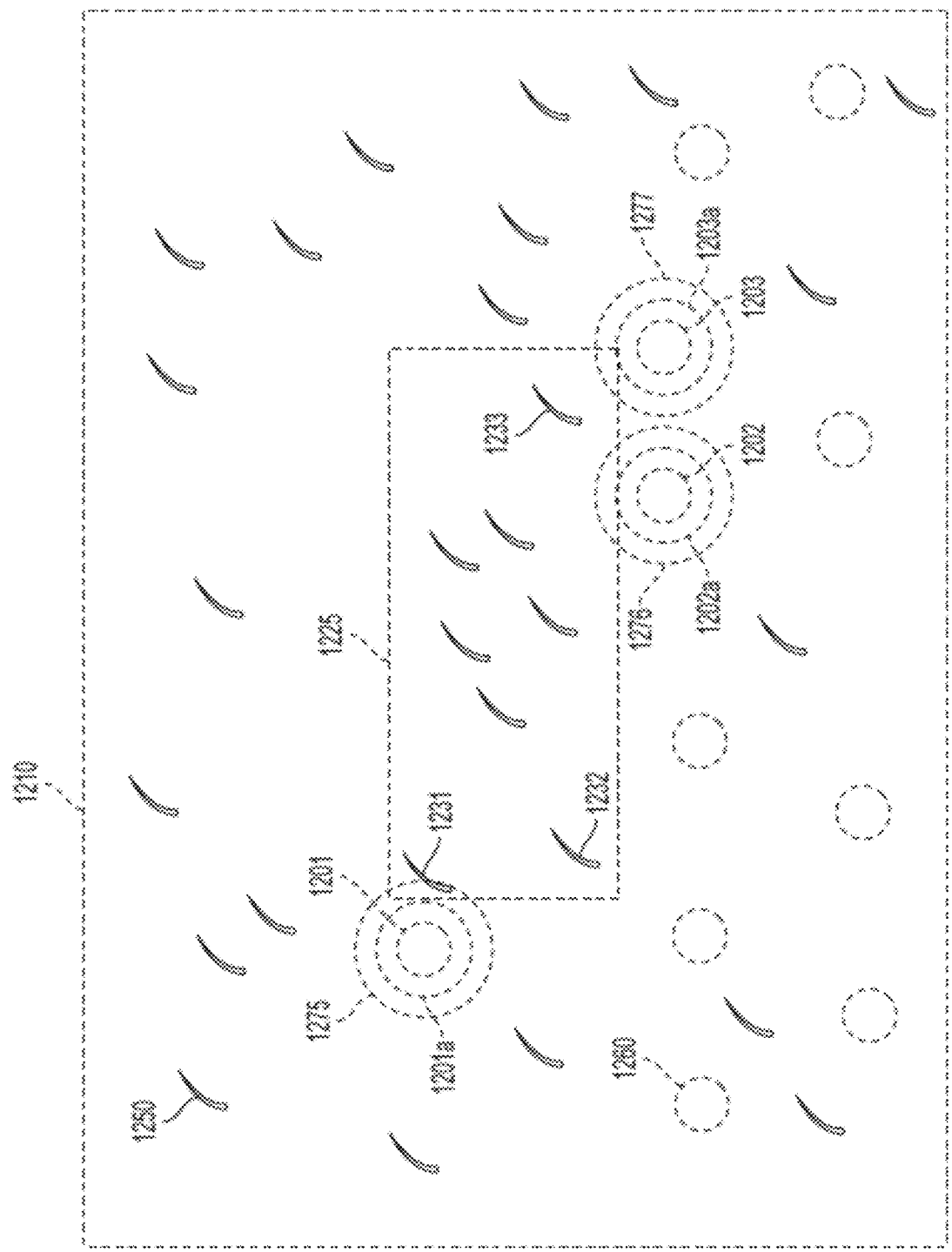

According to another method, such as the 'position-based' or 'position priority' method, a proximity band may be identified around previous harvesting sites. For example, in reference to FIG. 12E, if circular areas corresponding to the exclusion zone for previous harvesting sites have a 2 millimeter diameter, the proximity band may extend, for example, 1 millimeter beyond the exclusion zone corresponding to the respective previous harvesting site. Follicular unit harvesting candidates may then be selected if they are within a proximity band. However, although this example discusses exclusion zones as circularly shaped as shown in FIG. 12E, it is understood that this is an example only. In various implementations, exclusion zones may be shaped other than circles (including the shapes described and shown in reference to other Figures and embodiments) and proximity bands may extend an area outside various shaped exclusion zones accordingly.

Figure 12F:
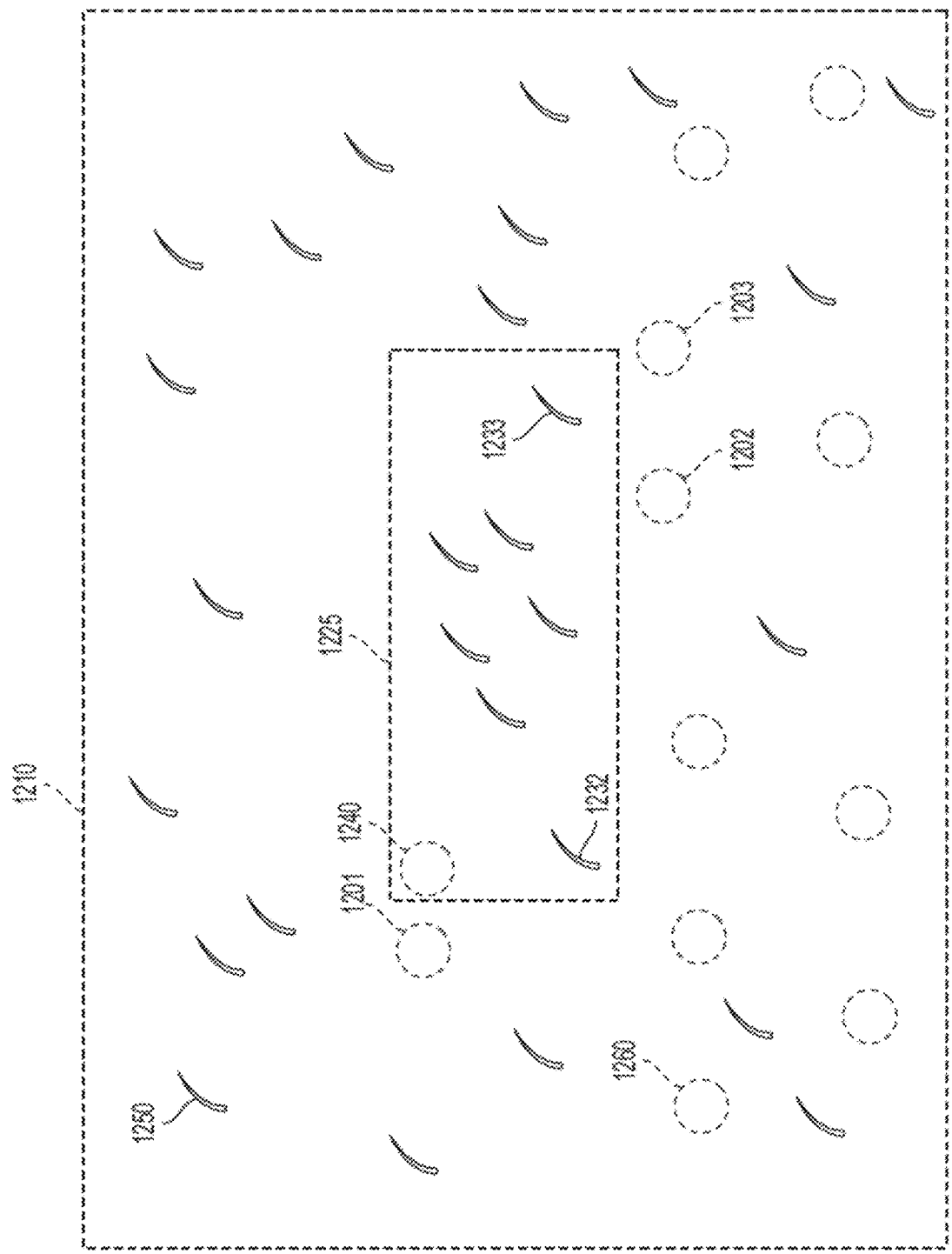

FIG. 12(e) illustrates proximity bands 1275, 1276, and 1277 around exclusion zones 1201a, 1202a, and 1203a of harvest sites 1201, 1202, and 1203, respectively. As FIG. 12(e) shows, only follicular unit harvesting candidate 1231 is located within any of the proximity bands (specifically, proximity band 1275). As such, the follicular unit harvesting candidate 1231 is selected for harvesting (as is shown in FIG. 12(f)).

However, in some instances, no follicular unit harvesting candidates may be located within a proximity band. In such an instance, a follicular unit harvesting candidate may be selected utilizing the lowest and closest method.

Further, in various instances, a number of follicular unit harvesting candidates may be located within proximity bands. In such instances, selection among follicular unit harvesting candidates located within one or more proximity bands may be performed utilizing various criteria. In some cases where a number of follicular unit harvesting candidates are located within proximity bands, a follicular unit harvesting candidate may be selected utilizing the lowest and closest method.

In another case, exclusion zones may be identified around previous harvest sites inside which follicular units will not be selected and potential exclusion zones for follicular unit harvesting candidates that are located in one or more proximity bands may also be identified. Overlap between the existing exclusion zones and the potential exclusion zones may then be analyzed to select follicular unit harvesting candidates within one or more proximity bands for selection (such as by the overlap priority method, the overlap priority lowest and closest method, the max overlap priority method, and so on). This extension to the position priority method may be referred to as the 'position-based overlap' or 'position priority overlap' method.

Additionally, though the position priority overlap method first determines follicular unit harvesting candidates that are located within proximity bands and then determines which of these have potential exclusion zones that overlap with existing exclusion zones, it is understood that this is for the purposes of example and is not intending to be limiting. In a 'overlap priority position' method, follicular unit harvesting candidates that have potential exclusion zones that overlap with existing exclusion zones may first be determines and then which of these are located within proximity bands may be determined.

The following example formula may be used to combine overlap-based and position-based methods:

$$\text{Objective} = \sum_{\text{if } distance(i) < 2*minDistance} (2*minDistance - \text{distance}(i))^2 - w*(\text{ratio}*Y + X)$$

In the above example formula, X and Y may be the relative distance in X and Y to a candidate follicular harvesting site. Ratio may be a factor defined to assign more weight in the formula to the X axis or the Y axis. W may be a weight to select between overlap priority or position priority methods. Regarding the term [−w*(ratio*Y+X)] of the formula, if a candidate follicular harvesting site is closer to a previous harvest site (smaller Y and X), this value will be large. However, if a candidate hair is further away (larger Y and X), this value will be small (possibly negative). Again, as stated above in the formula, the formula is useful when distance (i) is less than 2 times minDistance.

Yet other methods contemplated by the present disclosure may be 'pattern-based' or 'pattern priority' methods. For example, one such pattern-based method may be a 'triangular pattern-based' method or 'triangular pattern priority' method. In the triangular pattern priority method, for example, an equilateral triangle may be formed with a base of a triangle being a distance between two previous harvesting sites (e.g., distance "x"). An equilateral triangle is a triangle that includes sides of all the same length. Once a third point or apex of the equilateral triangle (other than two previous harvest sites) is determined, any hair that is positioned within a predetermined small distance (such as, for example, one half of "x") may be selected for harvesting. Alternatively, in other embodiments several triangles may be formed between two previous harvesting sites and available candidate follicular units. One triangle may be closer to an equilateral triangle than another triangle, even if neither has sides of all the same length, if the differences between the sides of the first triangle is smaller than the differences between the sides of the second triangle. For example, a first triangle with sides 5-6-7 is closer to an equilateral triangle than a second triangle with sides 5-14-22. Among available candidates, one would give priority to the candidate follicular units which forms triangle that is closest to the equilateral triangle than triangles formed by other candidates and previous harvesting sites.

Figure 12G:
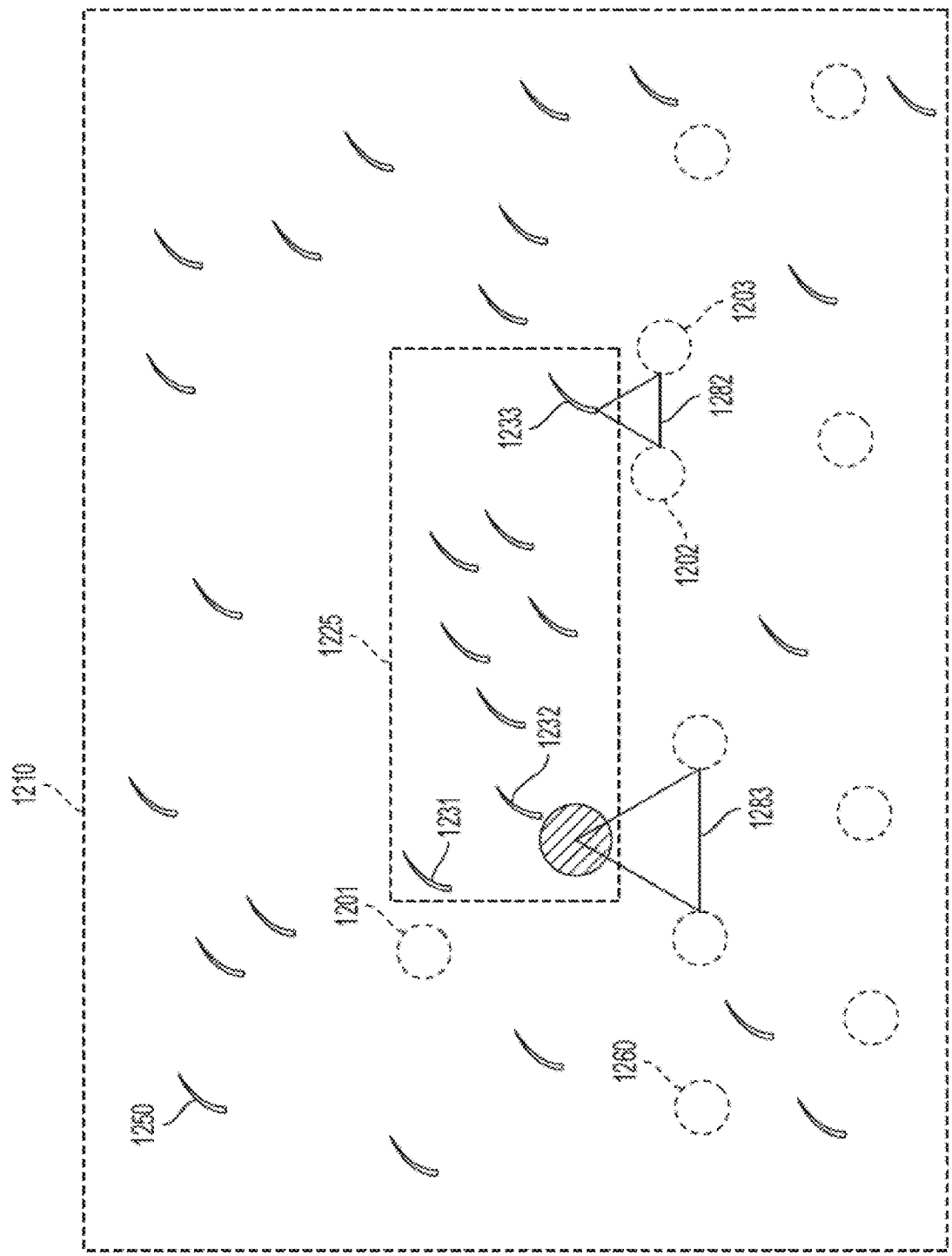
Figure 12H:
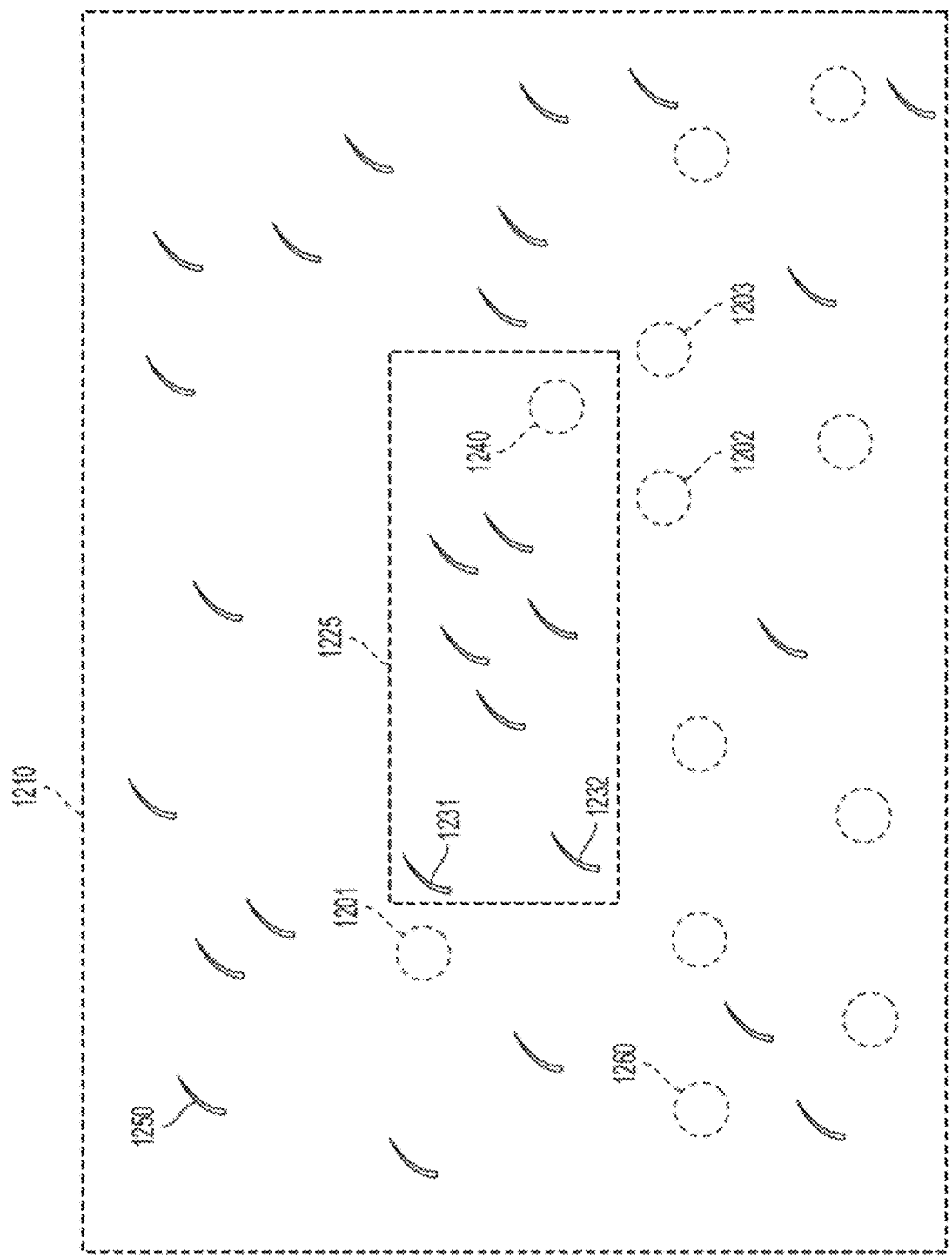

FIG. 12(g) illustrates equilateral triangles 1282 and 1283 respectively formed based on previous harvest sites. In the illustrated example, triangle 1283 is formed based on the distance between two previous harvesting sites, as shown. Any candidate follicular unit that is positioned, for example, within a certain small distance (which could be pre-determined, or selected by the user, and in some embodiments, may be a percentage of the distance between the two previous harvesting sites that formed the basis for the triangle) from an apex of such triangle may be selected for harvesting. As seen in FIG. 12(g), candidate follicular unit 1232 is not within a predetermined distance from the apex of the triangle (shown as shaded area), and therefore is not selected for harvesting. On the other hand, as FIG. 12(g) shows, follicular unit candidate 1233 is positioned close to or within a small distance from the apex of the equilateral triangle 1282. As such, follicular unit harvesting candidate 1233 is selected for harvesting (as is shown in FIG. 12(h)).

The following example formula may be used to determine triangles between follicular harvesting candidates and previous harvest sites:

$$\text{Objective} = (\text{distance}A - \text{minDistance})^2 + (\text{distance}B - \text{minDistance})^2$$

In the above example formula, distanceA (which may correspond to a line defined as a point C to a point A of a triangle) and distanceB (which may correspond to a line defined as point C to a point B) may be the two shortest distances from a candidate follicular harvesting site (corresponding to the point C) to previous harvest sites (corresponding to points B and A). If points A, B and C form a triangle with equal edge distances, minDistance may be close to both distanceA and distanceB.

However, in some instances, no triangle may be identified between follicular unit harvesting candidates and previous harvesting sites. In such an instance, a follicular unit harvesting candidate may be selected utilizing the lowest and closest method.

Further, in various instances, more than one follicular unit harvesting candidates may be positioned within a predetermined distance from the equilateral triangles, or correspond to triangles that are approximately equilateral triangles. In such instances, selection among follicular unit harvesting candidates that meet the above condition may be performed utilizing various criteria. In some cases a particular follicular unit harvesting candidate out of several follicular unit harvesting candidates that meet the above condition may be selected utilizing the lowest and closest method.

In another case, exclusion zones around previous harvest sites and potential exclusion zones for follicular unit harvesting candidates that correspond to triangles that are identically close to equilateral triangles may be identified. Overlap between the existing exclusion zones and the potential exclusion zones may then be analyzed to select follicular unit harvesting candidates that correspond to such triangles (such as by the overlap priority method, the overlap priority lowest and closest method, the max overlap priority method, and so on). This extension to the triangular pattern priority method may be referred to as the 'triangular pattern priority overlap' method.

In still another case, proximity bands may be identified around previous harvest sites and follicular unit harvesting candidates that correspond to triangles that are identically close to equilateral triangles may be selected if they are within a proximity band. This extension to the triangular pattern priority method may be referred to as the 'triangular pattern priority position' method.

In yet another case, exclusion zones around previous harvest sites and potential exclusion zones for follicular unit harvesting candidates that correspond to triangles that are identically close to equilateral triangles may be identified. Overlap between the existing exclusion zones and the potential exclusion zones may then be analyzed to select follicular unit harvesting candidates that correspond to such triangles (such as by the overlap priority method, the overlap priority lowest and closest method, the max overlap priority method, and so on). If multiple potential exclusion zones overlap existing exclusion zones, proximity bands may be identified around previous harvest sites and follicular unit harvesting candidates that correspond to the overlapping potential exclusion zones may be selected if they are within a proximity band. This extension to the triangular pattern priority method may be referred to as the 'triangular pattern priority overlap position' method.

In still another case, proximity bands may be identified around previous harvest sites and follicular unit harvesting candidates that correspond to triangles that are identically close to equilateral triangles may be selected if they are within a proximity band. If multiple follicular unit harvesting candidates are located within a proximity band, exclusion zones for previous harvest sites and potential exclusion zones for follicular unit harvesting candidates within a proximity band may be identified. If multiple follicular unit harvesting candidates are within a proximity band, exclusion zones around previous harvest sites and potential exclusion zones for follicular unit harvesting candidates within a proximity band may be identified. Overlap between the existing exclusion zones and the potential exclusion zones may then be analyzed to select follicular unit harvesting candidates that correspond to triangles and are within proximity bands (such as by the overlap priority method, the overlap priority lowest and closest method, the max overlap priority method, and so on). This extension to the triangular pattern priority method may be referred to as the 'triangular pattern priority position overlap' method.

Although the overlap priority method, position priority method, triangular pattern priority method, and various combinations of these methods are described above and illustrated in FIGS. 12(a)-12(h), it is understood that this is for the purposes of example. Any number of these and other methods may be combined in any order without departing from the scope of the present disclosure. Further, any of the above methods and/or any combination thereof may use the lowest and closest method when the respective method does not select any follicular unit harvesting candidates and/or when the respective method identifies multiple follicular unit harvesting candidates for selection.

Moreover, although FIGS. 12(a)-12(h) are illustrated and described above in the context of harvesting of follicular units, it is understood that this is for the purposes of example. The methods discussed herein may be utilized in the context of implanting follicular units and/or any other medical procedure.

It will be apparent that the number of steps that are utilized for such methods are not limited to those described above. Also, the methods do not require that all the described steps are present. Although the methodology described above as discrete steps, one or more steps may be added, combined or even deleted, without departing from the intended functionality of the embodiments of the invention. The steps can be performed in a different order or have the steps shared between more than one processor, for example. It will also be apparent that the method described above may be performed in a partially or substantially automated fashion, including performed using robotic systems.

As will be appreciated by those skilled in the art, the methods of the present invention may be embodied, at least in part, in software and carried out in a computer system or other data processing system. Therefore, in some exemplary embodiments hardware may be used in combination with software instructions to implement the present invention.

A machine-readable medium may be used to store software and data which causes the system to perform methods of the present invention. The above-mentioned machine-readable medium may include any suitable medium capable of storing and transmitting information in a form accessible by processing device, for example, one or more computers. Some examples of the machine-readable medium include, but not limited to, magnetic disc storage, flash memory device, optical storage, random access memory, etc.

Figure 11:
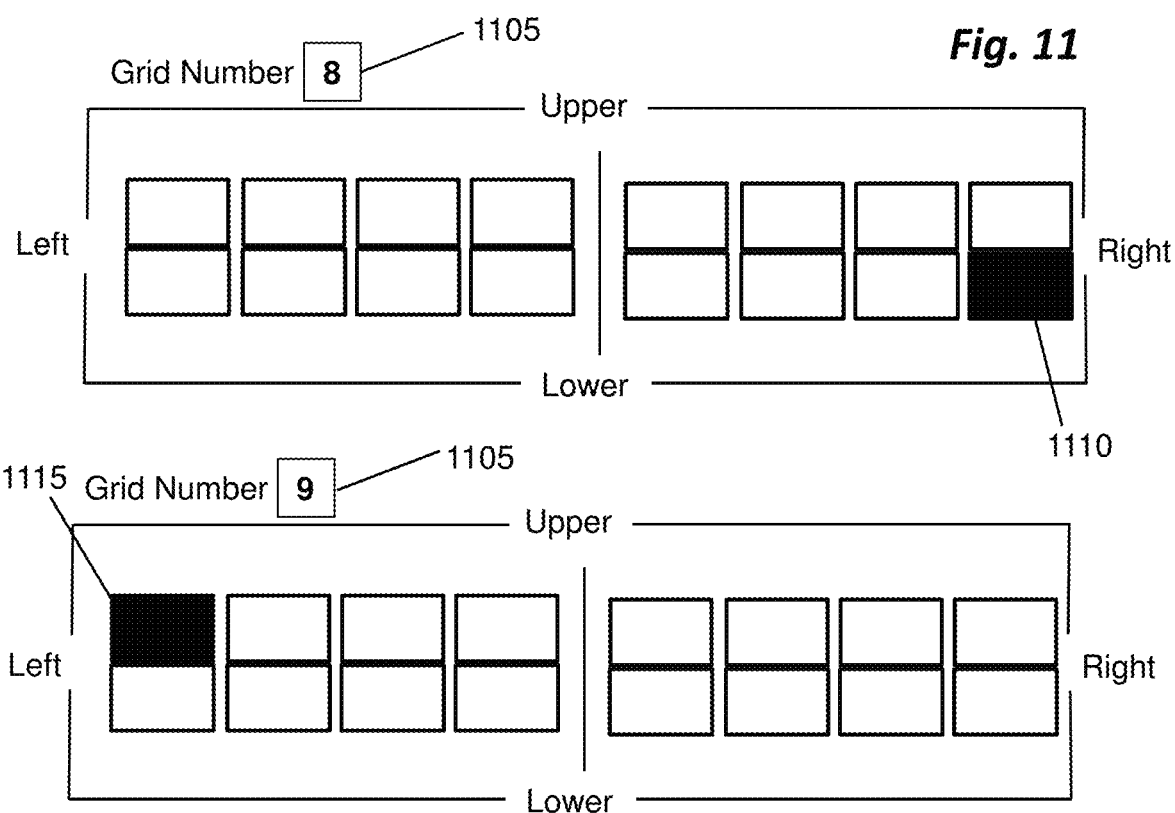
FIG. 11 is a schematic representation of an example of a grid that may be displayed on a monitor.

Certain procedures may require performing the same or similar operation on different areas or portions of the body surface. For example, an area of the body surface may be divided into several sections and a procedure performed on one or more sections at time, until the entire area has been covered. For example, during the hair transplantation procedure, a skin tensioner may be positioned in a series of positions on the patient's head, and the hair transplantation procedure performed in each of the series of positions. In the example of hair transplantation procedure, this series of positions may be configured to best suit the hair transplantation case in question, but may for example take the form of a grid with two rows and eight columns (four positions on each side of the head), as illustrated in FIG. 11. The user may place a skin tensioner on the patient's head, beginning at the left-hand low corner, move the grid across the patient's head in a series of moves, for example, 8 moves as shown in the example of FIG. 11, until the right-hand lower corner is reached, and then move up to a second row on the patient's head, but once again move from left to right, until all sixteen sections have been completed. The advantage of moving from left to right in this manner is that while follicular units are being harvested from grid 1115, the dissected follicular units can be removed from grid 1110, thereby increasing efficiency of the procedure. For user convenience to track which grids have had hair harvested from or implanted into them (or in other applications, grids or sections where certain procedure was performed), the monitor 240 can schematically display the regions to the user.

To enable the system to track which grid location on the patient's head is having the procedure carried out on, the user may be required to provide some sort of action to enable the system to correlate the grid locations, in the present example, on the patient's head to the grid locations on the computer monitor. One way in which the user can provide the identity of the grid location is by selecting the appropriate grid, for example 1110, on the display that corresponds to the location on the patient's head. Such selection may be provided by clicking of a mouse button, touching the monitor, or by using the up-, down-, left- and right-arrow keys of a keyboard, for example, or in any number of ways known to those skilled in the art. By doing this, the system is able to associate the placing of the skin tensioner in a particular location with a designated grid on the display. When the user has selected a grid location on the display, the system may also increment a grid number indicator 1105 on the monitor. For example, when selecting grid 1110, the grid number indicator may indicate that grid 8 has been chosen. The system may then be operated to identify the location of each of the fiducials on the skin tensioner, and to select a location from where the next hair follicle is to be harvested from, or determine a location into which the next hair follicle is to be implanted. When the desired hair has been harvested from or implanted into the area bound by the skin tensioner, for example, using robotic hair transplantation system, the user may move the skin tensioner to the next grid location, for example 1115, on the patient's head, (having first moved the robot to a safe location so the user can safely access the skin tensioner). Having done so, the user may once again identify to the system the new grid location 1115 on the display. The system will associate the positioning of the skin tensioner with grid 1115 on the display, and increments the grid number accordingly, in this case such that indicates grid 9 has been selected.

The use of grid numbers (in this case 8 and 9) can be used in a treatment report, and allow the physician to correlate dissection results to skin tensioner location on the patient's scalp. Knowing which parameters were used for any one grid location, the user can perhaps try and optimize the parameters used to provide for optimal harvesting results. In addition, this also allows the user to select certain parameters that may have been used to one particular grid, and apply them to another. For example, the user may set the system such that only every other hair that is visualized by the imaging system is harvested from grid location 8, and call that particular selection, harvest program 1. Rather than having to go through setting all the parameters again when the skin tensioner is moved to grid 9, the user may simply select the same harvesting program that was applied to grid 8, that is harvest program 1, and only every other hair that is visualized by the imaging system will be harvested from grid location 9.

The various embodiments described above are provided by way of illustration only and should not be construed to limit the claimed invention. These embodiments are susceptible to various modifications and alternative forms, and it should be understood that the invention generally, as well as the specific embodiments described herein, cover all modifications, equivalents and alternatives falling within the scope of the appended claims. By way of non-limiting example, it will be appreciated by those skilled in the art that particular features or characteristics described in reference to one figure or embodiment may be combined as suitable with features or characteristics described in another figure or embodiment. Further, those skilled in the art will recognize that the devices, systems, and methods disclosed herein are not limited to one field, such as hair restoration, but may be applied to any number of fields. The description, therefore, is not to be taken in a limiting sense, and the scope of the present invention is defined by the appended claims.

It will be further appreciated by those skilled in the art that the invention is not limited to the use of a particular system, and that automated (including robotic), semi-automated, and manual systems and apparatus may be used for positioning and actuating the respective removal tools and other devices and components disclosed herein. Applicant regards the subject matter of the invention to include all novel and nonobvious combinations and subcombinations of the various elements, features, functions, and/or properties disclosed herein.

What is claimed is:

1. A system for a performing a procedure on a body surface of a patient, the system comprising:
   a robotic arm that controls a position of a tool relative to a body surface of a patient during a procedure;
   a camera positioned to capture images of the body surface during the procedure; and
   a computing system coupled to the robotic arm and the camera, and configured to control the robotic arm during the procedure, said computing system programmed to:
   provide, on a display screen, a user interface that includes functionality for a user to view the images and to interactively control movement of the tool relative to the body surface during the procedure,
   identify a first site already operated upon with the tool;
   generate and display, on the user interface, a circular region centered on the center of the first site;
   create an exclusion zone surrounding a new potential operating site, the exclusion zone having a shape that extends a greater distance from the new potential operating site in a direction of penetration of the tool than in other directions;
   determine that the first site is in the exclusion zone, said user interface configured to display a visual representation of the exclusion zone on a displayed image of the body surface; and
   based on determining that the first site is in the exclusion zone, select an alternative new operating site on the body surface and reposition the exclusion zone such that the exclusion zone surrounds the alternative new operating site and extends a greater distance from the alternative new potential operating site in a direction of penetration of the tool than in other directions, wherein the alternative new operating site is selected such that the first site is outside the exclusion zone, the exclusion zone partially overlaps the generated and displayed circular region, and the alternative new operating site is outside the generated and displayed circular region.

2. The system of claim 1, wherein the tool is a harvesting tool, and the generated and displayed circular region defines an area surrounding a follicular unit harvesting site, from which no additional follicular units are to be harvested.

3. The system of claim 1, wherein the exclusion zone has a tear-drop shape.

4. The system of claim 1, wherein the tool is an implantation tool, and the generated and displayed circular region defines an area, surrounding an implantation site, in which no additional implantation sites are to be selected.

5. The system of claim 1, wherein the computing system is configured to use at least one user-specified parameter to select at least a size of the exclusion zone.

6. The system of claim 5, wherein the user-specified parameter defines a minimum distance between sites.

7. The system of claim 1, wherein the user interface visually depicts the exclusion zone by modifying a color of a corresponding portion of the displayed image.

8. The system of claim 1, wherein the computing system is programmed to automatically fill gaps between adjacent generated and displayed circular regions centered on centers of sites previously operated on.

9. The system of claim 1, wherein the computing system is programmed to display, on the displayed image of the body surface, a visual indication of a feature of the body surface to be operated on by the tool.

10. A non-transitory computer storage medium having stored thereon program instructions that direct a processor of a system to perform a process that comprises:
generating, on a display screen, a user interface that displays images of a body surface of a patient on which a procedure is being performed using a tool, the images captured by a camera;
identifying a location upon which the tool operates;
identifying a first site already operated upon with the tool;
generating and displaying a circular region centered on the center of the first site;
create an exclusion zone surrounding a new potential operating site, the exclusion zone having a shape that extends a greater distance from the new potential operating site in a direction of penetration of the tool than in other directions;
determine that the first site is in the exclusion zone;
displaying a visual representation of the exclusion zone on the display screen on a displayed image of the body surface; and
based on determining that the first site is in the exclusion zone, selecting an alternative new operating site on the body surface such that the first site is outside the exclusion zone and repositioning the exclusion zone such that the exclusion zone surrounds the alternative new operating site and extends a greater distance from the alternative new potential operating site in a direction of penetration of the tool than in other directions, wherein the alternative new operating site is selected such that the first site is outside the exclusion zone, the exclusion zone partially overlaps the generated and displayed circular region, and the alternative new operating site is outside the generated and displayed circular region.

11. The computer storage medium of claim 10, wherein the tool is a harvesting tool, and the generated and displayed circular region defines an area, encompassing a follicular unit harvesting site, from which no additional follicular units are to be harvested.

12. The computer storage medium of claim 10, wherein the shape of the exclusion zone is a tear-drop shape.

13. The computer storage medium of claim 10, wherein the tool is an implantation tool, and the generated and displayed circular region defines a region, surrounding an implantation site, in which no additional implantation sites are to be created.

14. The computer storage medium of claim 10, wherein the process comprises using at least one user-specified parameter to select at least a size of the exclusion zone.

15. The computer storage medium of claim 14, wherein the user-specified parameter specifies a minimum distance between sites.

16. The computer storage medium of claim 10, wherein displaying the visual representation of the exclusion zone comprises modifying a color of a corresponding portion of the displayed image.

17. The computer storage medium of claim 10, wherein the process comprises automatically filling gaps between adjacent circular regions centered on centers of sites previously operated on.

18. The computer storage medium of claim 10, wherein the process further comprises displaying, on the displayed image of the body surface, a visual indication of a next follicular unit to be harvested.

* * * * *